United States Patent
Muni et al.

(10) Patent No.: US 10,383,820 B2
(45) Date of Patent: *Aug. 20, 2019

(54) COLCHICINE DRUG-TO-DRUG INTERACTIONS

(71) Applicant: RxOMEG Therapeutics LLC, Woburn, MA (US)

(72) Inventors: Indu Muni, North Reading, MA (US); Naomi Vishnupad, Reading, MA (US)

(73) Assignee: RxOMEG Therapeutics LLC, Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/155,571

(22) Filed: Oct. 9, 2018

(65) Prior Publication Data

US 2019/0183793 A1    Jun. 20, 2019

Related U.S. Application Data

(63) Continuation of application No. 15/848,498, filed on Dec. 20, 2017.

(51) Int. Cl.
| | | |
|---|---|---|
| *A61K 31/165* | (2006.01) |
| *A61K 31/496* | (2006.01) |
| *A61P 29/00* | (2006.01) |
| *A61P 19/02* | (2006.01) |
| *A61K 31/403* | (2006.01) |
| *A61K 31/4422* | (2006.01) |
| *A61K 31/4709* | (2006.01) |
| *A61K 9/08* | (2006.01) |
| *A61K 9/00* | (2006.01) |
| *A61P 31/00* | (2006.01) |
| *A61K 47/02* | (2006.01) |
| *A61K 47/12* | (2006.01) |
| *A61K 47/36* | (2006.01) |
| *A61K 47/10* | (2017.01) |
| *A61K 47/26* | (2006.01) |

(52) U.S. Cl.
CPC .............. *A61K 9/08* (2013.01); *A61K 9/0053* (2013.01); *A61K 9/0095* (2013.01); *A61K 31/165* (2013.01); *A61K 31/403* (2013.01); *A61K 31/4422* (2013.01); *A61K 31/4709* (2013.01); *A61K 31/496* (2013.01); *A61K 47/02* (2013.01); *A61K 47/12* (2013.01); *A61K 47/36* (2013.01); *A61P 19/02* (2018.01); *A61P 29/00* (2018.01); *A61P 31/00* (2018.01); *A61K 47/10* (2013.01); *A61K 47/26* (2013.01)

(58) Field of Classification Search
None
See application file for complete search history.

(56) References Cited

U.S. PATENT DOCUMENTS

| | | |
|---|---|---|
| 5,668,154 A | 9/1997 | Fink et al. |
| 7,601,758 B1 | 10/2009 | Davis |
| 7,619,004 B1 | 11/2009 | Davis |
| 7,820,681 B1 | 10/2010 | Davis |
| 7,906,519 B2 | 3/2011 | Davis |
| 7,915,269 B2 | 3/2011 | Davis |
| 7,935,731 B2 | 5/2011 | Davis |
| 7,964,647 B2 | 6/2011 | Davis et al. |
| 7,964,648 B2 | 6/2011 | Davis |
| 7,981,938 B2 | 7/2011 | Davis |
| 8,093,297 B2 | 1/2012 | Davis |
| 8,097,655 B2 | 1/2012 | Davis |
| 8,440,722 B2 | 5/2013 | Davis |
| 8,927,607 B1 | 1/2015 | Ducharme |
| 9,555,029 B2 | 1/2017 | Ducharme |
| 9,907,751 B2 | 3/2018 | Muni et al. |
| 2003/0055029 A1 | 3/2003 | D'Amato et al. |
| 2009/0093548 A1* | 4/2009 | Davis ................. A61K 31/16 514/629 |
| 2010/0179169 A1 | 7/2010 | Davis |
| 2014/0107213 A1 | 4/2014 | Davis |
| 2015/0057359 A1 | 2/2015 | Ducharme |
| 2015/0094317 A1 | 4/2015 | Ducharme |
| 2015/0094318 A1 | 4/2015 | Ducharme |
| 2015/0094322 A1 | 4/2015 | Riel et al. |
| 2015/0094375 A1 | 4/2015 | Ducharme |
| 2015/0164831 A1 | 6/2015 | Roberts et al. |
| 2015/0196513 A1 | 7/2015 | Nidorf |
| 2015/0196514 A1 | 7/2015 | Nidorf |
| 2016/0354396 A1 | 12/2016 | Mahoney et al. |
| 2017/0258715 A1 | 9/2017 | Muni et al. |
| 2018/0092841 A1 | 4/2018 | Muni et al. |
| 2018/0098938 A1 | 4/2018 | Muni et al. |

FOREIGN PATENT DOCUMENTS

| | | |
|---|---|---|
| CN | 102872181 A | 1/2013 |
| WO | WO 2008/021666 A2 | 2/2008 |
| WO | WO 2009/133431 A1 | 11/2009 |

(Continued)

OTHER PUBLICATIONS

International Search Report and Written Opinion for Application No. PCT/US2017/021777 dated Jun. 21, 2017.
International Preliminary Report on Patentability for Application No. PCT/US2017/021777 dated Sep. 20, 2018.
[No Author Listed], Colchicine Injection, USP. Bedford Laboratories. 1999. 2 pages.
[No Author Listed], Colchicine Product Information. Cayman Chemicals. Dec. 5, 2011. 1 page.
[No Author Listed], Colchicine Product Information. Sigma-Aldrich, Inc. 2003. 2 pages.

(Continued)

*Primary Examiner* — Bong-Sook Baek
(74) *Attorney, Agent, or Firm* — Wolf, Greenfield & Sacks, P.C.

(57) ABSTRACT

The use of oral colchicine solutions in combination with other therapeutics, while minimizing toxic drug to drug interactions are described herein. Related compositions are also provided.

10 Claims, 3 Drawing Sheets

(56) References Cited

FOREIGN PATENT DOCUMENTS

| WO | WO 2013/149109 A1 | 10/2013 |
| WO | WO 2017/156392 A1 | 9/2017 |
| WO | WO 2018/200143 A2 | 11/2018 |

OTHER PUBLICATIONS

Artursson et al., Caco-2 monolayers in experimental and theoretical predictions of drug transport. Adv Drug Deliv Rev. Mar. 1, 2001;46(1-3):27-43. Review.

Habib et al., Influence of certain additives on the photostability of colchicine solutions+. Drug Development and Industrial Pharmacy. 1989; 15(11):1905-9.

Krishna et al., Effects of oral posaconazole on the pharmacokinetic properties of oral and intravenous midazolam: a phase I, randomized, open-label, crossover study in healthy volunteers. Clin Ther. Feb. 2009;31(2):286-98. doi: 10.1016/j.clinthera.2009.02.022.

Rask et al., Cochicine use in 6000 patients with disk disease & other related resistantly-painful spinal disorders. J of Neurolog & Orthopaedic Medicine & Surgery. Dec. 1989; 10(4):291-8.

Stewart et al., Comparison of intestinal permeabilities determined in multiple in vitro and in situ models: relationship to absorption in humans. Pharm Res. May 1995;12(5):693-9.

Yee, In vitro permeability across Caco-2 cells (colonic) can predict in vivo (small intestinal) absorption in man—fact or myth. Pharm Res. 1997; 14(6):763-3.

Yu et al., Biopharmaceutics classification system: the scientific basis for biowaiver extensions. Pharm Res. Jul. 2002;19(7):921-5.

International Search Report and Written Opinion for Application No. PCT/US2018/066943 dated Apr. 3, 2019.

* cited by examiner

COLCHICINE DRUG-TO-DRUG INTERACTIONS

RELATED APPLICATIONS

This Application is a continuation application which claims the benefit under 35 U.S.C. § 120 of U.S. application Ser. No. 15/848,498, entitled "COLCHICINE DRUG-TO-DRUG INTERACTIONS", filed on Dec. 20, 2017, which is herein incorporated by reference in its entirety.

BACKGROUND OF THE INVENTION

Colchicine is an alkaloid compound found in plant extracts that is used to treat diseases such as gout, familial Mediterranean fever (FMF), pericarditis, Behçet's disease, atrial fibrillation, amyloidosis, calcium pyrophosphate deposition disease (pseudogout), cirrhosis of the liver, sarcoid arthritis, and inflammatory diseases.

Colchicine has been marketed for decades as a solid oral dosage form, such as a tablet administered to patients once or twice a day. Single-ingredient colchicine tablets (0.6 mg dosage strength) were available in the United States for decades as marketed but unapproved products. The first FDA approved single-ingredient oral colchicine product was Mutual Pharmaceutical's colchicine 0.6 mg tablets (Colcrys®, NDA 022352), which was approved in July 2009 for treatment of familial Mediterranean Fever, and treatment of acute flares of gout; approval for the prophylactic treatment of gout was granted in October 2009. Mitigare® (colchicine) Capsules (NDA 024820) was also approved for the prophylactic treatment of gout in 2014 based on the FDA finding of safety and efficacy for the probenecid-colchicine combination product.

SUMMARY OF THE INVENTION

The invention in some aspects is a pharmaceutical solution or suspension suitable for oral administration comprising colchicine and a pharmaceutically acceptable solvent system in combination with one or more other drugs.

In some aspects the invention is a method of treating a colchicine sensitive disorder, by orally co-administering a liquid colchicine solution and a P-gp inhibitor to a human subject having a colchicine sensitive disorder in an effective amount to treat the disorder.

In some embodiments the P-gp inhibitor is carvedilol phosphate. In some embodiments the dose of colchicine is 0.5-1.2 mg/dose/day. In some embodiments the dose of carvedilol phosphate is 10-80 mg/dose/day. In other embodiments there is no significant effect on colchicine blood levels when the liquid colchicine solution is taken in conjunction with carvedilol phosphate. In some embodiments after administration of a 0.6 mg (0.12 mg/mL, 5 mL) liquid colchicine solution to human subjects, with a multiple oral doses of carvedilol phosphate extended-release capsule, 40 mg the Cmax of colchicine is substantially similar to the Cmax of colchicine administered alone under the same conditions. In yet other embodiments after administration of a 0.6 mg (0.12 mg/mL, 5 mL) liquid colchicine solution to human subjects, with oral doses of carvedilol phosphate extended-release capsule, 40 mg the 90% CIs for Cmax, $AUC_{0-last}$ and $AUC_{0-inf}$ are contained within the 80.00 to 125.00% limits.

In other aspects the invention is a method of treating a colchicine sensitive disorder, by orally co-administering a liquid colchicine solution and a CYP3A4 inhibitor to a human subject having a colchicine sensitive disorder in an effective amount to treat the disorder.

In some embodiments the CYP3A4 inhibitor is a strong CYP3A4 inhibitor, such as posaconazole. In some embodiments the dose of posaconazole is 300-600 mg/dose/day. In other embodiments the dose liquid colchicine solution is reduced to 2 mL/day when coadministered with posaconazole. In some embodiments there is a 3 fold increase in colchicine blood levels when posaconazole is co-administered with liquid colchicine solution.

In some embodiments after administration of a 0.6 mg (0.12 mg/mL, 5 mL) liquid colchicine solution to human subjects, with oral doses of posaconazole the $C_{max}$ of colchicine is significantly higher than the $C_{max}$ of colchicine administered alone under the same conditions. In yet other embodiments after administration of a 0.6 mg (0.12 mg/mL, 5 mL) liquid colchicine solution to human subjects, with posaconazole the 90% CI's for $C_{max}$ and $AUC_{0-last}$ fell outside the 80 to 125% boundaries for bioequivalence. In some embodiments mean colchicine $C_{max}$ values are elevated by at least 2 fold from approximately 2.0 ng/mL (alone) to approximately 4.7 ng/mL (with posaconazole).

In some embodiments the CYP3A4 inhibitor is a weak CYP3A4 inhibitor, such as amlodipine besylate. In other embodiments the dose of amlodipine besylate is 5-10 mg/dose/day. In some embodiments there is no significant effect on colchicine blood levels when liquid colchicine solution is taken in conjunction with amlodipine besylate.

In some embodiments after administration of a 0.6 mg (0.12 mg/mL, 5 mL) liquid colchicine solution to human subjects, with amlodipine besylate the $C_{max}$ of colchicine is slightly higher than the $C_{max}$ of colchicine administered alone under the same conditions. In yet other embodiments after administration of a 0.6 mg (0.12 mg/mL, 5 mL) liquid colchicine solution to human subjects, with amlodipine besylate the upper 90% CI's for $C_{max}$, $AUC_{0\ last}$ and $AUC_{0-inf}$ fell outside the 80 to 125% boundaries for bioequivalence.

In some embodiments the CYP3A4 inhibitor is a moderate CYP3A4 inhibitor, such as ciprofloxacin hydrochloride. In some embodiments the dose of ciprofloxacin hydrochloride is 20-750 mg/dose/day. In some embodiments there is no significant effect on colchicine blood levels when liquid colchicine solution is taken in conjunction with ciprofloxacin hydrochloride. In some embodiments the dose of colchicine is 0.5-1.2 mg/dose/day.

In some embodiments after administration of a 0.6 mg (0.12 mg/mL, 5 mL) liquid colchicine solution to human subjects, with a ciprofloxacin hydrochloride the $C_{max}$ of colchicine is substantially similar to the $C_{max}$ of colchicine administered alone under the same conditions. In yet other embodiments after administration of a 0.6 mg (0.12 mg/mL, 5 mL) liquid colchicine solution to human subjects, with ciprofloxacin hydrochloride the 90% CIs for $C_{max}$, $AUC_{0-last}$ and $AUC_{0-inf}$ are contained within the 80.00 to 125.00% limits.

The invention in some aspects is a method of treating a colchicine sensitive disorder, by orally administering a liquid colchicine solution to a human subject having a colchicine sensitive disorder in an effective amount to treat the disorder, wherein the safety profile for the liquid colchicine solution is lower than the safety profile of a tablet or capsule colchicine formulation that is administered to a human subject having a colchicine sensitive disorder. In some embodiments the bioavailability is similar between the liquid colchicine solution and the tablet or capsule colchicine formulation, based on a Caco2 study. In some embodiments the safety profile is measured in terms of adverse events and wherein the liquid colchicine solution results in fewer adverse events than the tablet or capsule colchicine formulation. In some embodiments the colchicine sensitive disorder is selected from gout, prophylactic treatment of gout, familial Mediterranean fever (FMF), prophylactic treatment of FMF, pericarditis, prophylactic treatment of pericarditis, Behçet's disease, atrial fibrillation, prophylactic treatment of atrial fibrillation, amyloidosis, calcium pyrophosphate deposition disease (pseudogout), cirrhosis of the liver, sarcoid arthritis, inflammatory diseases, and disc diseases and related spinal disorders.

In other embodiments the methods further comprise a step of monitoring the subject for colchicine adverse events.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

The figures are illustrative only and are not required for enablement of the invention disclosed herein.

DETAILED DESCRIPTION

Figure 1:
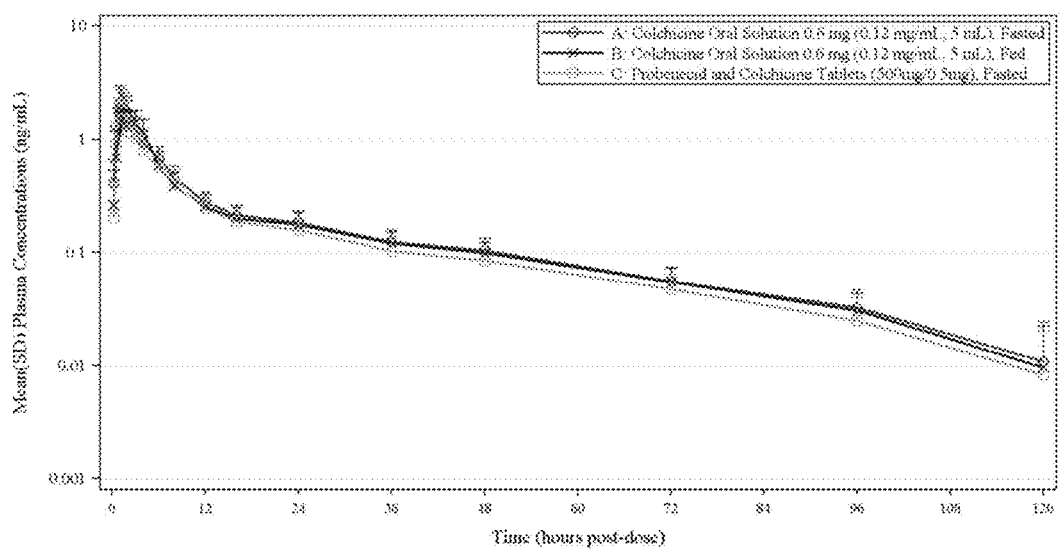
FIG. 1 is a graph depicting a determination of mean (SD) colchicine plasma concentrations (ng/mL) vs. time (Semi-log Scale)—PK Population in human clinical study 1 (Example 1).

Colchicine is administered to patients as a solid oral dosage form, such as a tablet or capsule. The development of liquid oral solutions of colchicine have not progressed because of the instability of the colchicine in a liquid formulation. Solutions having reasonable shelf life have not been developed. For instance, an article published in Drug Development and Industrial Pharmacy, 15(11), 1905-1909 (1989) by Habib, et. al., investigated the stability of colchicine and showed that there is photodegradation of colchicine in solution, especially in the presence of glycerin. Other additives, such as lithium carbonate, p-aminobenzoic acid, and uric acid, used in this study did not prevent the degradation of the colchicine, and furthermore, are not acceptable excipients for an oral solution.

It was discovered quite surprisingly that liquid solutions of colchicine for oral administration are stable at ambient temperature and have stable pH for extended periods of time. It was also discovered that oral solutions caused significantly fewer adverse events in human patients relative to tablets or capsules. Even with the fewer adverse events, these solutions result in similar blood levels of colchicine in patients to those produced by tablets and capsules.

Thus, the invention encompasses liquid formulations of colchicine, also referred to herein as colchicine oral solutions. The colchicine oral solutions have enhanced properties such as fewer adverse events, enhanced stability sufficient for significant shelf life and improved properties when used in combination with other drugs. Adverse events, as used herein, refers to any undesirable experience associated with the use of one or more medical products in a patient which is associated with the use and/or testing of the medical product, and may also be referred to herein as toxicity.

Applicant has conducted several human clinical trials on the liquid colchicine solution and has demonstrated that the solution has several advantages over the tablet or capsule formulations of colchicine. As shown in the Examples below, Applicant has conducted clinical trials on humans, including a comparative bioavailability study, including a food-effect arm, and multiple drug-drug interaction (DDI) studies [including studies with a P-gp inhibitor and three CYP3A4 inhibitors (strong, moderate and weak)]. Applicant has also demonstrated comparable permeability and/or bioavailability of the Colchicine Oral Solution (i.e. liquid colchicine solution of the invention) vs. marketed colchicine products (tablets and capsules) in an in vitro Caco-2 study. Applicant has also demonstrated comparable bioavailability and fewer adverse events in in vivo human clinical studies with the Colchicine Oral Solution when compared to published studies of marketed colchicine tablets and capsules.

Although it was found that the liquid solutions have comparable permeability and bioavailability, it was found quite surprisingly, that when liquid colchicine formulations are co-administered with several drugs which normally cause drug to drug interactions with colchicine, the combinations have been demonstrated to be within safety limits for co-administration.

Drug to drug interactions occur when multiple drugs are administered simultaneously or at staggered administration times and can affect the activity of one or both of the drugs. Interaction between the drugs in question is classified as pharmacodynamics drug interaction, whereby there is a change in sensitivity, etc., to the drug at its site of action, and pharmacokinetic drug interaction, where there is a change in the in vivo kinetics of the drug. With respect to the latter, clinically, the in vivo kinetics of a drug is still unknown and even when it is known, unexpected results occur when drugs are combined. Pharmacokinetic drug interaction sometimes develop because the drugs themselves compete for one route (enzymes, carriers, etc.) when drugs that use the same routes in terms of drugs absorption, distribution, metabolism or excretion are used concomitantly.

Information on drug interactions with colchicine has been well-established in the decades the active ingredient has been used in FDA-approved products. There are numerous studies and references that advise physicians to monitor patients on colchicine when taken concomitantly with drugs that interact with CYP3A4 and/or P-glycoprotein (P-gp).

Since colchicine is metabolized by cytochrome P450 (CYP) 3A4 demethylation in the liver, it may interact with substrates of this enzyme system, including estrogen, steroids, dapsone, diltiazem, erythromycin, lidocaine, lovastatin (and most other statins), midazolam, quinidine, terfenadine, testosterone, nifedipine, and verapamil. It may also be affected by inhibitors of this enzyme system, such as diltiazem, gestodene, grapefruit juice, ketoconazole, toleadomycin, and erythromycin.

P-glycoprotein modulators or substrates that may interact with colchicine include morphine, doxorubicin, vinblastine, vincristine, paclitaxel, digoxin, quinidine, amprenavir, indinavir, nelfinavir, ritonavir, saquinavir, loperamide, josamycin, erythromycin, clarithromycin, cyclosporine, aldosterone, dexamethasone, prednisolone, progesterone, verapamil, talinolol, fexofenadine, cimetidine, amitriptyline, nortriptyline, phenytoin, and simvastatin.

Administration of colchicine with macrolide antibiotics such as clarithromycin has been shown to impair colchicine elimination, resulting in excess drug accumulation. Acute myopathy has been reported when colchicine is used with pravastatin. Rhabdomylosis has been reported when colchicine was used with atorvastatin.

In order to determine whether colchicine oral solution had similar drug to drug interactions with drugs competing for the same pathways as colchicine delivered in tablets and capsules, several drug interactions studies were conducted with colchicine oral solution. Because colchicine is a substrate of the CYP3A4 metabolizing enzyme and the efflux transporter P-gp, the pharmacokinetics of Colchicine Oral Solution were evaluated following administration with posaconazole (a strong CYP3A4 inhibitor), ciprofloxacin hydrochloride (a moderate CYP3A4 inhibitor), amlodipine besylate (a weak CYP3A4 inhibitor) and carvedilol phosphate (a P-gp inhibitor). None of these drugs has been administered together with colchicine in any type of formulation to examine drug to drug interactions in scientifically valid/credible studies prior to the invention. Prior to the data generated according to the invention it was not predictable how these drugs would affect one another.

Colchicine oral solution was well-tolerated in the first study when administered as a single oral 0.6-mg dose alone and in combination with multiple doses of Coreg CR® (carvedilol phosphate) Extended-Release Capsules (P-gp inhibitor). Given that colchicine is a known substrate for P-gp, it was hypothesized that an inhibitor of P-gp such as carvedilol phosphate could potentially affect the PK profile of colchicine. In this study, it was surprisingly demonstrated that carvedilol phosphate had no effect on the $C_{max}$ of colchicine. The percent GMR of $AUC_{0-last}$ (co-administration with carvedilol phosphate/colchicine alone) was 117.9% and its 90% CI was in the range of 112.0%-124.1%. The 90% CIs for $C_{max}$, $AUC_{0-last}$ and $AUC_{0-inf}$ were contained within the 80 to 125% boundaries. The results suggest that colchicine oral solution can be used together with carvedilol phosphate at usual single drug doses, without adjustments.

Similar to the study with carvedilol phosphate, colchicine oral solution was well tolerated in the study with CYP3A4 inhibitors when administered as a single, oral, 0.6-mg dose alone and in combination. Colchicine oral solution was administered with multiple doses of posaconazole (strong CYP3A4 inhibitor), ciprofloxacin hydrochloride (moderate CYP3A4 inhibitor) and amlodipine besylate (weak CYP3A4 inhibitor). Ciprofloxacin hydrochloride (moderate CYP3A4 inhibitor) and amlodipine besylate (weak CYP3A4 inhibitor) had only minimal effects on the $C_{max}$ of colchicine. The effect was clinically small and dose adjustment for colchicine is not necessary when colchicine is co-administered with the amlodipine besylate or ciprofloxacin hydrochloride.

However, the combination of colchicine+posaconazole (strong CYP3A4 inhibitor) resulted in a surprisingly high increase in colchicine blood levels-greater than 3 fold increase. This increase was unexpected as some previously reported studies with other strong CYP3A4 inhibitors co-administered with solid dosage forms of colchicine did not show this increase. Furthermore this drug interaction has never been demonstrated with a colchicine oral liquid formulation. As result the dose of the drugs should be adjusted when colchicine+posaconazole are administered together.

Colchicine plasma levels were markedly elevated when colchicine oral solution was administered with a strong CYP3A4 inhibitor (i.e., posaconazole). There were no significant effects when colchicine oral solution was coadministered with a moderate CYP3A inhibitor (i.e., ciprofloxacin hydrochloride) a weak CYP3A inhibitor (i.e., amlodipine besylate) or a P-gp inhibitor (i.e., carvedilol phosphate).

In addition to the drug to drug interactions, colchicine is known to be a relatively toxic drug. It was discovered herein that colchicine caused fewer adverse events when delivered as a liquid solution than as a tablet or capsule. The data from the bioavailability studies described herein showed that the administration of liquid oral colchicine was associated with only 0.1% adverse events/study subject. In contrast to this, published studies have shown that Mitigare® (colchicine) Capsules are associated with 1.19% adverse events/study subject and Colcrys® tablets are associated with 0.33% adverse events/study subject.

Additionally, when colchicine oral solution was administered in combination with CYP (strong, moderate and weak) or P-gp inhibitors in the DDI studies, quite surprisingly, the incidence of TEAEs did not increase and there were no treatment related discontinuations. There were no statistically significant or clinically meaningful changes from baseline in hematology, clinical chemistry, vitals, ECG or urine analysis seen in any of studies, no serious adverse events (SAEs) were reported.

Thus, in some embodiments the drug product is a ready-to-use colchicine solution for oral administration. The formulation may contain 0.01-1.0 mg/mL of colchicine. For a 0.12 mg/mL formulation, the recommended dose is 5 mL to deliver a once or twice daily (maximum dose of 1.2 mg/day for some indications such as gout).

Colchicine, N-((7S)-5,6,7,9-tetrahydro-1,2,3,10-tetramethoxy-9-oxobenzo(a)heptalen-7-yl)-acetamide (CAS No. 64-86-8), is a pale yellow powder soluble in water in 1:25 dilution, having a pH in solution of 5.9 and a pK of 12.35 at 20° C. Colchicine is an alkaloid found in extracts of certain plants such as *Colchicum autumnale* and *Gloriosa superba*. Colchicine arrests cell division in animals and plants. It has adversely affected spermatogenesis in humans and in some animal species under certain conditions.

As used herein, "colchicine" refers to colchicine base, its salt, or solvate or derivative or isomer or polymorph thereof. Suitable compounds include the free base, the organic or inorganic salts, isomers, isomer salts, solvates, polymorphs, complexes, etc. Colchicine has the following structure:

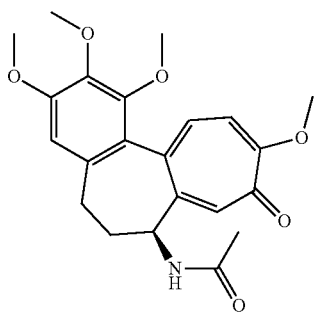 [SMILES: COc1cc2c(c(OC)c1OC)-c1ccc(OC)c(=O)cc1[C@@H](NC(C)=O)CC2]

Also provided herein are methods of treating gout, familial Mediterranean fever (FMF), Behçet's disease, cardiovascular disease (atrial fibrillation, pericarditis), amyloidosis, calcium pyrophosphate deposition disease (pseudogout), cirrhosis of the liver, sarcoid arthritis, inflammatory diseases, and Disc diseases & related spinal disorders comprising administering to a patient, such as a child or an elderly patient, an oral liquid formulation comprising colchicine as described herein. In some embodiments, oral liquid formulations disclosed herein can also be used to treat for other conditions (e.g., skin conditions) known in the art (Ben-Chetrit E, Levy M. Colchicine: 1998 update. Semin Arthritis Rheum. 1998; Yurdakul S, Mat C, Tuiziin Y, Ozyazgan Y, Hamuryudan V, Uysal O, Senocak M, Yazici H. A double-blind trial of colchicine in Behçet's syndrome. Arthritis Rheum. 2001 November; 44(11):2686-92. August; 28(1): 48-59; Molad Y. Update on colchicine and its mechanism of action. Curr Rheumatol Rep. 2002 June; 4(3):252-6).

Commonly, geriatric populations encounter difficulty being administered solid oral dosage forms such as tablets and capsules. This may lead to non-compliance with the recommended pharmacotherapy with the solid oral dosage forms and likely results in rendering the therapy ineffective. Solid oral dosage forms are usually not favorable for geriatric populations due to the potential risk of choking. Additionally, certain solid oral dosage forms of medications cannot be administered simply by crushing (e.g., patients requiring various types of feeding tubes) because of the coating or drug delivery mechanism by which the drug is released.

In some embodiments the oral liquid colchicine formulation is stable at room temperature for at least 3 months, at least 6 months, at least 18 months, or at least 24 months. In some embodiments the oral liquid colchicine formulation is stable at accelerated temperatures for at least 1 month, at least 2 months, at least 3 months, or at least 6 months. In some embodiments the oral liquid colchicine formulation is determined to be stable when the solution has less than 5%, less than 4%, less than 3%, less than 2%, less than 1% or less than 0.5% of any one degradant. In other embodiments the oral liquid colchicine formulation is determined to be stable when the solution has less than 5%, less than 4%, less than 3%, less than 2%, less than 1% or less than 0.5% of total degradants. In some embodiments, degradants include 3 lumicolchicine, γ-lumicolchicine, colchiceine, and any other individual unknown impurities.

Currently colchicine is primarily used to treat patients suffering from gout. An oral liquid formulation can provide physicians more flexibility in designing dosage regimens for their patients. This is particularly important since colchicine is toxic and has a narrow therapeutic index. The methods described herein are useful for the treatment of gout. The treatment of gout involves the prophylactic treatment of gout as well as the treatment of acute out flares. The prophylactic treatment of gout refers to the treatment of a patient who has had one or more gout flares, in order to reduce the occurrence of future gout flares.

Gout (or gouty arthritis) is a disease caused by a build-up of uric acid due to an overproduction of uric acid or a reduced ability of the kidney to get rid of uric acid. It is more common in males, postmenopausal women, and people with high blood pressure. Heavy alcohol use, diabetes, obesity, sickle cell anemia, and kidney disease also increase the risk. The condition may also develop in people who take drugs that interfere with uric acid excretion.

In gout, monosodium urate or uric acid crystals are deposited on the articular cartilage of joints, tendons and surrounding tissues due to elevated concentrations of uric acid in the blood stream. This provokes an inflammatory reaction of these tissues. Gout is characterized by excruciating, sudden, unexpected, burning pain, as well as swelling, redness, warmness, and stiffness in the affected joint. Low-grade fever may also be present. The patient usually suffers from two sources of pain. The crystals inside the joint cause intense pain upon action or movement of the affected area. The inflammation of the tissues around the joint also causes the skin to be swollen, tender and sore if it is even slightly touched. Acute gouty arthritis (alternatively referred to as a gout flare or a gout attack) is a sudden attack of pain in affected joints, especially in the feet and legs. Chronic gout involves repeated attacks of joint pain.

In acute gouty arthritis, symptoms develop suddenly and usually involve only one or a few joints. The big toe, knee, or ankle joints are most often affected. The pain frequently starts during the night and is often described as throbbing, crushing, or excruciating. The joint appears infected with signs of warmth, redness, and tenderness. The attacks of painful joints may go away in several days, but may return from time to time. Subsequent attacks usually last longer. Some people may progress to chronic gout (chronic gouty arthritis), while others may have no further attacks.

If several attacks of gout occur each year, it can lead to joint deformity and limited motion in joints. Uric acid deposits, called tophi, develop in cartilage tissue, tendons, and soft tissues. These tophi usually develop only after a patient has suffered from the disease for many years. Deposits also can occur in the kidneys, leading to chronic kidney failure.

Colchicine can be used for treating adults with acute gouty arthritis and pain in attacks of acute gouty arthritis, and also can be used beneficially for treating adults with chronic gout for prophylaxis of acute gout flares. Although its exact mode of action in the relief of gout is not completely understood, colchicine is known to decrease the inflammatory response to urate crystal deposition by inhibiting migration of leukocytes, to interfere with urate deposition by decreasing lactic acid production by leukocytes, to interfere with kinin formation and to diminish phagocytosis and the subsequent anti-inflammatory response. The anti-inflammatory effect of colchicine is relatively selective for acute gouty arthritis. However, other types of arthritis occasionally respond. It is neither an analgesic nor a uricosuric and will not prevent progression to chronic gouty arthritis. It does have a prophylactic, suppressive effect that helps to reduce the incidence of acute attacks and to relieve the residual pain and mild discomfort that patients with gout occasionally experienced. In some instances, non-steroidal anti-inflammatory drugs (NSAIDs) may also be prescribed to relieve pain and inflammation in acute gouty arthritis attacks. Strong painkillers, such as codeine, or corticosteroids may also be prescribed to relieve the pain.

Colchicine is rapidly absorbed from the gastrointestinal tract. Peak concentrations occur in 0.5 to 2 hours. The drug and its metabolites are distributed in leukocytes, kidneys, liver, spleen and the intestinal tract. Colchicine is metabolized in the liver and excreted primarily in the feces with 10 to 20% eliminated unchanged in the urine. In some embodiments, oral liquid formulations disclosed herein are used to treat gout.

Familial Mediterranean Fever (FMF) is a recessively inherited disorder characterized by dramatic episodes of fever, serosal inflammation and abdominal pain. This inflammatory disorder is episodic, with self-limited bouts of fever accompanied by unexplained arthritis, sterile peritonitis, pleurisy and/or skin rash. Patients often develop progressive systemic amyloidosis from the deposition of the acute phase reactant serum amyloid A (SAA). In some patients, progressive systemic amyloidosis can lead to kidney failure and death. The factors which incite an episode are unclear. In some embodiments, colchicine can be prescribed as an anti-inflammatory therapy.

FMF is observed primarily in individuals of non-Ashkenazi Jewish, Armenian, Arab and Turkish background. Although rare in the United States, incidence of FMF in Middle Eastern populations can be as high as 1:7 in Armenian populations and 1:5 in non-Ashkenazi Jewish populations.

FMF attacks are characterized by a massive influx of polymorphonuclear leukocytes (PMNs) into the affected anatomic compartment. At the biochemical level, patients have been reported to have abnormal levels of C5a inhibitor (Matzner and Brzezinski, "C5a-inhibitor deficiency in peritoneal fluids from patients with familial Mediterranean fever," *N. Engl. J. Med.*, 311:287-290 (1984)), neutrophil-stimulatory dihydroxy fatty acids (Aisen et al, "Circulating hydroxy fatty acids in familial Mediterranean fever," *Proc. Natl. Acad. Sci. USA*, 2:1232-1236 (1985)), and dopamine β-hydroxylase (Barakat et al, "Plasma dopamine beta-hydroxylase: rapid diagnostic test for recurrent hereditary polyserositis," *Lancet*, 2:1280-1283 (1988)). Although linkage studies have placed the gene causing FMF (designated MEFV) on chromosome 16p (Pras et al., "Mapping of a gene causing familial Mediterranean fever to the short arm of chromosome 16," *N. Engl. J. Med.*, 326:1509-1513 (1992); Shohat et al., "The gene for familial Mediterranean fever in both Armenians and non-Ashkenazi Jews is linked to the α-globin complex on 16p: evidence for locus homogeneity," *Am. J. Hum. Genet.*, 51:1349-1354 (1992); Pras et al, "The gene causing familial Mediterranean fever maps to the short arm of chromosome 16 in Druze and Moslem Arab families," *Hum. Genet.*, 94:576-577(1994); French FMF Consortium, "Localization of the familial Mediterranean fever gene (FMF) to a 250 kb-interval in non-Ashkenazi Jewish founder haplotypes," *Am. J. Hum. Genet.*, 59:603-612 (1996)), the genetic basis of FMF has not previously been identified. In some embodiments, oral liquid formulations disclosed herein are used to treat FMF.

Behcet's disease is a chronic multisystem disease characterized by oral and genital aphthae, arthritis, cutaneous lesions, and ocular, gastrointestinal, and neurologic manifestations. It was first described by the Turkish dermatologist Hulusi Behcet in 1937 as "recurrent oral aphthous ulcers, genital ulcers, and 'hypopyon-uveitis.'" The diagnosis of Behcet's disease is based on clinical criteria as established by O'Duffy and Goldstein and the International Study Group. Complex aphthosis is the presence of almost constant, multiple oral or oral and genital aphthae in the absence of systemic manifestations. These patients must be distinguished from those with Behcet's disease. Colchicine has been used as a treatment for Behcet's disease through its ability to inhibit of neutrophil functions (Hirohata et al., Behçet's disease. Arthritis Res Ther 2003 5:139 DOI: 10.1186/ar757). In some embodiments, oral liquid formulations disclosed herein are used to treat Behçet's Disease.

The prevalence of Behcet's disease is higher in the Middle East and Japan where it is approximately 1 in 1000. The disease is far less common in northern Europe, the United States, and the United Kingdom. The mean age of onset ranges from the mid to late 20s to the fourth decade, according to several series, with a slightly higher male to female ratio. It is relatively rare in children and the elderly. Behcet's disease is also uncommon among black Africans who, when they are affected, tend to have more mucocutaneous features. Although a definitive pattern of inheritance has not been elucidated, familial cases have been reported. Patients with complex aphthosis are probably a subset of patients with recurrent aphthous stomatitis, which is defined as the recurrence of 1 or more painful oral ulcers at intervals ranging from days to months. The prevalence of recurrent aphthosis ranges from 5% to 66%. Onset may occur in childhood or adolescence and some patients experience a decrease in frequency with advancing age. (source: J. V Ghate and J. L. Jorizzo, "Behcet's disease and complex aphthosis", Journal of the American Academy of Dermatology, 1999, 40(1), 1-18.)

Cardiovascular disease (CVD) involves the heart of blood vessels. CVD includes, but is not limited to coronary artery diseases (CAD), stroke, hypertensive heart disease, rheumatic heart disease, cardiomyopathy, atrial fibrillation, congenital heart disease, endocarditis, pericarditis, aortic aneurysms, peripheral artery disease, and venous thrombosis.

One very typical and dangerous arrhythmia is atrial fibrillation (AFIB). AFIB is the most common cardiac arrhythmia resulting in hospitalization in the United States. AFIB is identified by irregular heart rhythms and is clinically defined as uncoordinated contractions of the atria. Patients often experience palpitations and have an increased risk of stroke. Some patients may be asymptomatic. Approximately one-third of all strokes are due to AFIB. Furthermore, the presence of AFIB makes strokes 5-times more likely and 2-times more debilitating.

The role of colchicine in inflammation, microtubule disruption, adhesion of neutrophils, and other qualities, makes it a promising treatment for some cardiovascular diseases (Deftereos et al., Colchicine and the Heart: pushing the envelope. J Am Coll Cardiol. 2013; 62(20):1817-1825. doi:10.1016/j.jacc.2013.08.726; Tong et al., Colchicine in cardiovascular disease: an ancient drug with modern tricks. 2016 Heart doi: 10.1136/heartjnl-2015-309211). In some embodiments, oral liquid formulations disclosed herein are used to treat cardiovascular diseases (e.g., atrial fibrillation and pericarditis).

Amyloidosis is a rare and potentially fatal disease that can be either localized or systemic. There are four major types of amyloidosis. The four major types include immunoglobulin (primary) amyloidosis, reactive (secondary) amyloidosis, beta-2 microglobulin amyloidosis and hereditary amyloidosis. Each different type of amyloidosis presents a different prognosis and stems from different underlining conditions. The pathologic features of amyloid deposits include beta-pleated sheet structures that are composed of amyloid fibrils with diameters between 8 to 10 nm. Beta-pleated sheets can be viewed under polarized light after being stained using Congo Red stain, these stained fibrils display an apple green birefringence.

Secondary amyloidosis is associated with chronic inflammatory diseases such as FMF. The precursor protein responsible for constructing the amyloid fibrils associated with secondary amyloidosis is serum amyloid A, an acute-phase reactant. Typical sites of amyloid accumulation include the spleen, liver, lymph nodes, adrenal glands, and the kidneys. Symptoms that are nonspecific include complaints of weakness and fatigue. Specific complaints are directly associated to organ involvement, these symptoms commonly include edema and pain. In some embodiments, oral liquid formulations disclosed herein are used to treat amyloidosis.

Calcium pyrophosphate deposition disease (CPDD), also known as pseudogout, chondrocalcinosis, and pyrophosphate arthropathy, is a rheumatologic disorder with varied symptoms and signs arising from the accumulation of crystals of calcium pyrophosphate dihydrate in the connective tissues.

Pseudogout refers to the acute symptoms of joint inflammation or synovitis: red, tender, and swollen joints that may resemble gouty arthritis. The disorder is more common in older adults. It may be asymptomatic, or it can be associated with osteoarthritis, or it can present as an acute or chronic inflammatory arthritis that causes pain in one or more joints. The white blood cell count is often raised.

The arthritis is usually polyarticular (inflammation of several joints in the body), although it may begin as mono-articular (one joint). CPPD crystals tend to form within articular tissues. Knees are the most commonly affected joints, along with wrists and hips. In rare cases, pseudogout may affect the spinal canal and cause damage to the spinal cord. In some embodiments, oral liquid formulations disclosed herein are used to treat pseudogout.

Cirrhosis, a condition in which the liver does not function properly due to long-term damage, typically comes on slowly over months or years. Early on, there are often no symptoms. As the disease worsens, a subject may become tired, weak, itchy, have swelling in the lower legs, develop yellow skin, bruise easily, have fluid build-up in the abdomen, or develop spider-like blood vessels on the skin. The fluid build-up in the abdomen may become spontaneously infected. Other complications include hepatic encephalopathy, bleeding from dilated veins in the esophagus or dilated stomach veins, and liver cancer. Hepatic encephalopathy results in confusion and possibly unconsciousness. Colchicine has been shown to have anti-fibrotic effects in relation to hepatic diseases (Leung et al., Colchicine—Update on mechanisms of action and therapeutic uses. 2015. Seminar in Arthritis and Rheumatism. 45 (3), 257-67).

Cirrhosis is most commonly caused by alcohol, hepatitis B, hepatitis C, and non-alcoholic fatty liver disease. Typically, more than two or three drinks per day over a number of years is required for alcoholic cirrhosis to occur. Non-alcoholic fatty liver disease is due to a number of reasons, including being overweight, diabetes, high blood fats, and high blood pressure. A number of less common causes include autoimmune hepatitis, primary biliary cirrhosis, hemochromatosis, certain medications, and gallstones. Cirrhosis is characterized by the replacement of normal liver tissue by scar tissue. These changes lead to loss of liver function. Diagnosis is based on blood testing, medical imaging, and liver biopsy. In some embodiments, oral liquid formulations disclosed herein are used to treat hepatic diseases (e.g., cirrhosis of the liver).

Sarcoidosis, a disease involving abnormal collections of inflammatory cells, can be involved with the joints, bones and muscles. This causes a wide variety of musculoskeletal complaints that act through different mechanisms. Approximately 5-15% of cases affect the bones, joints, or muscles.

Sarcoid arthritis has two classifications: acute or chronic. Sarcoidosis patients with acute arthritis often also accompanies bilateral Hilar lymphadenopathy and Erythema nodosum. Usually true arthritis is not present, but instead peri-arthritis presents itself as a swelling in the soft tissue around the joints that can be seen by ultrasonographic methods. These joint symptoms tend to precede or occur at the same time as erythema nodosum develops. Enthesitis also occurs in about one-third of patients with acute sarcoid arthritis, mainly affecting the Achilles tendon and heels. Soft tissue swelling at the ankles can be prominent, and biopsy of this soft tissue reveals no granulomas, but does show panniculitis that is similar to erythema nodosum.

Chronic sarcoid arthritis usually occurs in the setting of more diffuse organ involvement. The ankles, knees, wrists, elbows, and hands may all be affected in the chronic form and often in a polyarticular pattern. Dactylitis similar to that seen in Psoriatic arthritis, that is associated with pain, swelling, overlying skin erythema, and underlying bony changes may also occur. In some embodiments, oral liquid formulations disclosed herein are used to treat sarcoid arthritis.

Disc diseases & related spinal disorders are a group of disorders that are quite painful. It is believed that colchicine acts directly on diskal inflammation to reduce inflammation in the area surrounding the spinal nerve roots. Colchicine has also been shown to cause an increase of endorphin-producing neurons in the spinal cord and to prevent deposition of amyloid in damaged disc. In some embodiments the subject has diskal back pain and or sciatica. In some embodiments, oral liquid formulations disclosed herein are used to treat disc diseases and related spinal disorders.

The liquid formulations described herein may include additional ingredients. For instance these additional components may include, but are not limited to, buffering agents, preservatives, sweeteners, flavoring agents, glycols such as propylene glycol and glycerin, as examples, and coloring agents. Additional excipients such as tonicity agents and chelating agents are within the scope of the embodiments.

Buffering agents maintain the pH when colchicine is formulated into a liquid form. Non-limiting examples of buffering agents include, but are not limited to, sodium bicarbonate, potassium bicarbonate, magnesium hydroxide, magnesium lactate, magnesium gluconate, aluminum hydroxide, aluminum hydroxide/sodium bicarbonate precipitate, a mixture of an amino acid and a buffer, a mixture of aluminum glycinate and a buffer, a mixture of acid salt and an amino acid and a buffer, and a mixture of an alkali salt of an amino acid and a buffer. Additional buffering agents include citric acid, sodium citrate, sodium tartarate, sodium acetate, sodium carbonate, sodium polyphosphate, potassium polyphosphate, sodium pyrophosphate, potassium pyrophosphate, disodium hydrogen phosphate, dibasic sodium phosphate, trisodium phosphate, tripotassium phosphate, sodium acetate, potassium metaphosphate, magnesium oxide, magnesium carbonate, magnesium silicate, calcium acetate, calcium glycerophosphate, calcium chloride, calcium hydroxide, calcium lactate, calcium carbonate, calcium bicarbonate, and other calcium salts. Some buffering agents also impart effervescent qualities when a powder is incorporated into a liquid. In some embodiments, the colchicine described herein, when formulated into a liquid form, comprises a buffering agent.

Preservatives include anti-microbials, anti-oxidants, and agents that enhance sterility. Exemplary preservatives include ascorbic acid, ascorbyl palmitate, benzyl alcohol, BHA, BHT, citric acid, erythorbic acid, fumaric acid, malic acid, propyl gallate, sodium ascorbate, sodium benzoate, sodium bisulfate, sodium metabisulfite, sodium sulfite, parabens (methyl-, ethyl-, butyl-), benzoic acid, potassium sorbate, and vanillin. In some embodiments, the colchicine described herein, when formulated into a liquid form, comprises a preservative.

Sweeteners or sweetening agents include any compounds that provide a sweet taste to make the product more palatable. This includes natural and synthetic sugars, natural and artificial sweeteners (e.g., sucralose), natural extracts and any material that initiates a sweet sensation in a subject. In some embodiments, the colchicine described herein, when compounded into a liquid form, comprises a sweetener. In other embodiments, sweeteners in liquid form are used to solvate or dissolve the colchicine described herein.

Sugars illustratively include glucose, fructose, sucrose, xylitol, tagatose, maltitol, isomaltulose, lactitol, sorbitol, mannitol, erythritol, trehalose, maltodextrin, polydextrose, and the like. Other sweeteners include glycerin, inulin, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrosylates, maltitol syrup, high fructose corn syrup, and as branded proprietary blend products. Sweeteners can be used singly or combinations of two or more. Suitable concentrations of different sweeteners can be selected based on published information, manufacturers' data sheets, and by routine testing. In certain instances, an above-described flavored solution component is used to solvate or dissolves colchicine described herein.

In another embodiment, the liquid form comprises a flavoring agent or flavorant to enhance the taste or aroma of the solution component used to solvate or dissolve the colchicine described herein. Suitable natural or synthetic flavoring agents can be selected from standard reference books, such as Remington: The Science and Practice of Pharmacy (2000) and Fenaroli's Handbook of Flavor Ingredients (1994). Non-limiting examples of suitable natural flavors, some of which can be readily simulated with synthetic agents or combinations thereof, include almond, anise, apple, apricot, banana, blackberry, blackcurrant, blueberry, caramel, cherry, chocolate, cinnamon, cranberry, grape, lemon, lime, orange, peppermint, pineapple, raspberry, spearmint, strawberry, vanilla, etc. Also useful, particularly where the composition is intended primarily for pediatric use is tutti-frutti or bubble gum flavor, a compounded flavoring agent based on fruit flavors. Presently, preferred flavoring agents include bubble gum, strawberry, cherry, grape, orange, peppermint, and vanilla. In some embodiments, the resultant liquid form from the colchicine described herein comprises a Flavor Cherry 825.662 flavoring agent. Flavoring agents may be used singly or in combinations of two or more.

In further embodiments, the resultant liquid form from the colchicine described herein comprises a coloring agent for identity and/or aesthetic purposes. Suitable coloring agents approved by the U.S. Food and Drug Administration (FDA) include FD&C Red No. 3, FD&C Red No. 20, FD&C Red No. 40, FD&C Yellow No. 6, FD&C Blue No. 2, D&C Green No. 5, D&C Orange No. 5, D&C Yellow No. 10, caramel, ferric oxide and mixtures thereof.

In further embodiments, the resultant liquid form from the colchicine described herein comprises a thickening agent. Thickening agents include, but are not limited to xanthan gum.

In some embodiments other flavoring agents, buffering systems, and preservatives may be used. The solution is formulated to inhibit growth of bacteria, mold, and yeast for storage at room temperature and ambient conditions.

In some embodiments, the liquid formulation includes 0.2-0.4% w/v of benzyl alcohol, 0.1-0.3% w/v of anhydrous citric acid, 0.005-0.025% w/v of colchicine, 0.005-0.02% w/v of dye, 0.8-1.6% w/v or dibasic sodium phosphate, heptahydrate, 0.75-0.15% w/v of flavor 825.662, 2-8% w/v of propylene glycol, 2-10% glycerin, 0.1-0.2% w/v of sweetener, 0.1-0.2% w/v of xanthan gum, and water. In other embodiments, the formulation includes 0.28-3.2 or 0.3% w/v of benzyl alcohol, 0.2% w/v of anhydrous citric acids, 0.012% w/v of colchicine, 0.01% w/v of FD&C Red No. 40, 1.2% w/v or dibasic sodium phosphate, heptahydrate, 0.125% w/v of flavor cherry 825.662, 5% w/v of propylene glycol, 0.15% w/v of sucralose, 0.15% w/v of xanthan gum, and water.

An exemplary formulation includes benzyl alcohol (0.3% w/v), Citric Acid (0.2% w/v), dye (0.01% w/v), Dibasic Sodium Phosphate, Heptahydrate (0.125% w/v), propylene glycol (5% w/v), glycerin (5% w/v), sweetener (0.15% w/v), xanthan gum (0.15% w/v), and water. The formulation may include Colchicine (0.012% w/v).

The colchicine described herein is stable in various storage conditions including refrigerated, ambient, and accelerated conditions. Stable as used herein refers to the ability of an active agent to maintain activity under standard stability conditions. Standard stability conditions include relative humidity conditions along with the temperatures, 25 degrees C. 60% RH(RT), 30 C 65% RH (ICH), and 40 C 75% RH (accelerated), for example.

At refrigerated and ambient conditions, the liquid colchicine composition described herein in stable for at least 1 month, at least 2 months, at least 3 months, at least 6 months, at least 9 months, at least 12 months, at least 15 months, at least 18 months, and at least 24 months. At accelerated conditions, the colchicine solution described herein is stable for at least 1 month, at least 2 months, at least 3 months and at least 6 months. Accelerated conditions include temperatures that are above ambient levels. In some instances, an accelerated condition is at about 30° C., about 35° C., about 40° C., about 45° C., about 50° C., about 55° C., or about 60° C. Ambient conditions include temperature that is at ambient levels. In some instances, an ambient condition is at about 20° C., about 21° C., about 22° C., C, a t 23 bout 24° C., about 25° C., about 26° C., about 27° C., about 28° C., about 29° C., and about 30° C. Refrigerated conditions include temperature in typical refrigeration units (e.g. 5±+3° C.). In some instances, a refrigerated condition is about 2° C., about 3° C., about 4° C., about 5° C., about 6° C., about 7° C., or about 8° C.

Liquid vehicles suitable for the colchicine described herein are selected for a particular oral liquid composition (e.g., solution, suspension, etc.) as well as other properties such as clarity, viscosity, compatibility with excipients, chemical inertness, palatability, odor, and color. Exemplary liquid vehicles include water, ethyl alcohol, glycerin, propylene glycol, syrup (e.g., sugar or other sweetener based, e.g., Ora-Sweet® SF sugar-free flavored syrup), juices (e.g., apple, orange, cranberry, cherry, tomato and the like), other beverages (e.g., tea, coffee, soft drinks, milk and the like), oils (e.g., olive, soybean, corn, mineral, castor and the like), and combinations or mixtures thereof. Certain liquid vehicles, e.g., oil and water, can be combined together to form emulsions. In some embodiments, water is used as a vehicle for a colchicine oral liquid. In other embodiments, propylene glycol is used as a vehicle for a colchicine oral liquid. For the liquid colchicine described herein, the solution component is used as the vehicle for a colchicine oral liquid.

The viscosity of the solution is an important component. In some embodiments the solution has a viscosity in the range of 40-800 cps. In other embodiments the solution has a viscosity of 80-250 cps.

The colchicine oral liquid compositions may be used for the treatment of diseases and conditions described herein. In addition, a method for treating any of the diseases or conditions described herein in a subject in need of such treatment involves administration of colchicine oral liquid compositions in therapeutically effective amounts to the subject. In some embodiments, the amount of a given colchicine oral liquid composition that corresponds to such an amount varies depending on factors such as the particular colchicine salt or form, disease condition and its severity, the identity (age, weight, sex) of the subject or patient in need of treatment, but can nevertheless be determined according to the particular circumstances surrounding the case, including, e.g., the specific agent being administered, the liquid composition type, the condition being treated, and the subject or patient being treated.

In further embodiments, the daily dosages appropriate for the colchicine oral liquid compositions described herein are from about 0.5 mg-2.4 mg/day, or in other embodiments 0.2 mg-1.5 mg/dose/day or in other embodiments 0.5 mg-1.5 mg/dose/day. In one embodiment, the daily dosage appropriate for the colchicine liquid compositions is about 0.6-1.2 mg/dose/day.

Typically, daily dosages should be considered when colchicine oral solution is co-administered with other drugs, particularly CYP3A4 or PgP-glycoprotien inhibitors. Typically, the daily dosage of the posaconazole (a strong CYP3A4 inhibitor) dose is 300 mg/day to 600 mg/day. A first dose of 300 mg on the first day followed by a second dose on the first day may be administered. In some embodiments the daily dose delivered after the first day is 300 mg/day. The tablets are available as 100 mg tablets, and multiple tablets may be administered at a time. The daily dosage for a moderate CYP3A4 inhibitor such as ciprofloxacin hydrochloride is generally one 500 mg Cipro® (ciprofloxacin hydrochloride. The daily dosage for a weak CYP3A4 inhibitor such as amlodipine besylate is typically 5 mg once daily with a maximum dose of 10 mg once daily. The daily dosage for a moderate P-gp inhibitor such as carvedilol phosphate is generally a single daily oral dose of Coreg CR® (carvedilol phosphate) Extended Release Capsule, 20 mg.

The treatment of certain diseases or conditions (e.g., gout, FMF, cardiac disease etc.) in a patient or subject with a colchicine oral liquid composition described herein encompass additional therapies and treatment agents in some embodiments. Such additional therapies and treatment regimens include another therapy, e.g., antibiotics, for the treatment of the particular disease in some embodiments.

Unless defined otherwise, all technical and scientific terms used herein have the same meanings as commonly understood by one of ordinary skill in the art. Although any methods and materials similar or equivalent to those described herein can be used in the practice of testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or". The terms "comprise", "have", and "include" are open-ended linking verbs. Any forms or tenses of one or more of these verbs "comprises," "comprising," "has," "having," "includes," and "including" are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent such as oral colchicine is directed to the treatment and/or the amelioration of, reversal of, or stabilization of the symptoms of gout, familial Mediterranean fever (FMF), pericarditis, Behçet's disease, atrial fibrillation, amyloidosis, calcium pyrophosphate deposition disease (pseudogout), cirrhosis of the liver, sarcoid arthritis, and inflammatory diseases described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with an oral colchicine composition, can include, but is not limited to, providing an oral colchicine composition into or onto the target tissue; providing an oral colchicine composition systemically to a patient by, e.g., oral administration whereby the therapeutic reaches the target tissue or cells. "Administering" a composition may be accomplished by injection, topical administration, and oral administration or by other methods alone or in combination with other known techniques.

As used herein, the terms "patient," "subject" and "individual" are intended to include living organisms in which certain conditions as described herein can occur. The term patient, as used herein, refers to human patients. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In certain instances, the human is elderly. In other instances, the human is 65 years of age or older. Other examples of subjects include experimental animals such as mice, rats, dogs, cats, goats, sheep, pigs, and cows. By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology).

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1: Study-001; a Randomized, Open-Label, Single-Dose, 3-Way, Relative Bioavailability Human Clinical Study The study examined the bioavailability of Colchicine Oral Solution 0.6 mg (0.12 mg/mL, 5 mL) under Fed and Fasted Conditions in comparison to Probenecid and Colchicine Tablets, USP (500 mg/0.5 mg) under Fasted Conditions in Healthy Adult Volunteers The primary study objectives included: 1) determining the relative bioavailability of Colchicine Oral Solution 0.6 mg (0.12 mg/mL, 5 mL) and Probenecid and Colchicine Tablets, USP (500 mg/0.5 mg) under fasted conditions in healthy adult male and female volunteers; and 2) assessing the effect of food on the absorption of Colchicine Oral Solution 0.6 mg (0.12 mg/mL, 5 mL) by administration of the formulation under fed versus fasted conditions in healthy adult male and female volunteers. Secondary study objections included the evaluation and comparison of the safety and tolerability of single oral doses of Colchicine Oral Solution 0.6 mg (0.12 mg/mL, 5 mL) and Probenecid and Colchicine Tablets, USP (500 mg/0.5 mg) in healthy adult male and female volunteers.

Methods:

This was an open-label, single dose, randomized, three-period, crossover design study to evaluate the relative bioavailability of a single oral dose of Colchicine Oral Solution 0.6 mg (0.12 mg/mL, 5 mL) and a single oral dose of one Probenecid and Colchicine Tablets, USP (500 mg/0.5 mg) under fasted conditions in healthy male and female subjects. Furthermore, the study evaluated the food effect of a single oral dose of Colchicine Oral Solution 0.6 mg (0.12 mg/mL, 5 mL) under fed and fasted conditions. Following a screening period of up to 21 days, a total of 36 healthy, non-smoking, adult, male and female subjects were enrolled. Total study participation was approximately 37 days (excluding up to 21 of screening). During this time, subjects were confined to the Clinical Research Unit (CRU) for 3 study periods for approximately 4 days (3 nights) on each period.

Eligible subjects received single oral doses of one of three study drugs (Treatment A, B or C) on three separate Periods in a randomly assigned sequence, with each treatment separated by an approximate 14-day washout period. In each study period (Day 1 of Periods 1, 2 and 3), dosing occurred in the morning after an overnight fast of at least 10 hours. For study drug administered under fasted conditions, subjects received their assigned dose of study drug after an overnight fast. Study medication was administered with 240 mL water.
- A: Test (Fasted): Single oral dose of Colchicine Oral Solution 0.6 mg (0.12 mg/mL, 5 mL) under fasted conditions
- B: Test (Fed): Single oral dose of Colchicine Oral Solution 0.6 mg (0.12 mg/mL, 5 mL) under fed conditions
- C: Reference (Fasted): Single oral dose of Probenecid and Colchicine Tablets, USP (500 mg/0.5 mg) under fasted conditions For study drug administered under fed conditions, subjects were given a high-fat, high-calorie (HFHC) meal after an overnight fast of at least 10 hours; each subject started consuming this meal 30 minutes prior to study drug administration and completed the entire meal at least 5 minutes prior to dosing. Study drug was then administered with 240 mL of water.

Each subject was randomized to one of three treatment sequences (ABC, BCA, CAB) with 12 subjects per sequence, according to a randomization schedule prepared prior to the start of the study (Period 1, 2 and 3). During each of the 3 study periods, confinement began at approximately 1400 hours on the day prior to dosing and continued until after the 48 h pharmacokinetic (PK) post dose sampling and safety assessments. Subjects were allowed to exit the CRU and then return on an outpatient basis for the 72 h, 96 h and 120 h PK sampling and safety assessments.

Fed Conditions Dosing Session: Following an overnight fast of at least 10 hours, subjects began consuming a HFHC breakfast approximately 30 minutes prior to dosing and completely consumed the meal approximately 5 minutes prior to dosing. Subjects then received a single oral dose of their assigned study drug with approximately 240 mL room temperature water at approximately 0800 hours (±1 hour).

Fasted Conditions Dosing Sessions: Following an overnight fast of at least 10 hours, subjects received a single oral dose of their assigned study drug with approximately 240 mL room temperature water at approximately 0800 hours (±1 hour).

In each of the 3 study periods, serial PK blood samples to measure plasma concentrations of colchicine were collected by direct venipuncture or by use of an indwelling catheter prior to dosing (up to 60 minutes prior to dosing) and at, 0.25, 0.5, 1, 1.25, 1.5, 1.75, 2, 2.5, 3, 4, 6, 8, 12, 16, 24, 36, 48, 72, 96 and 120 hours post dose. Where PK sampling time points coincide with vital sign measurements, vital signs were collected within 10 minutes prior to the scheduled time point, and PK samples were obtained at the scheduled time point.

Height and weight were measured and body mass index (BMI) was calculated at Screening. A full physical examination (PE) was performed at Screening, and an abbreviated PE was performed at the Check-in Visit of each Period and at the Study Exit/Early Termination Visit. PEs were repeated prior to study discharge as deemed necessary by the Investigator or in response to adverse events (AEs).

Pharmacokinetic Assessments:

Plasma concentrations of colchicine was measured. Pharmacokinetic parameters for colchicine including $C_{max}$, $t_{max}$, $AUC_{0-t}$, $AUC_{0-inf}$, $K_{el}$ and $t_{1/2}$ were calculated using a non-compartmental analysis method. Statistical Methods and Data Analysis Two analysis populations were used to summarize the results from this study.

Safety/Toxicity (Adverse Events) Population:

All subjects who received at least one dose of study drug were assessed.

PK Population:

All subjects who completed all three treatment periods without any major protocol violations, who had sufficient plasma colchicine concentration data for reliable estimates of the key pharmacokinetic variables, and who did not vomit within 3 hours of dosing.

The primary PK endpoints were maximum plasma colchicine concentration ($C_{max}$) and area under the plasma drug concentration versus time curve calculated to the last measurable observation ($AUC_{0-t}$). Secondary PK endpoints were dose-normalized AUC extrapolated to infinity ($AUC_{0-inf}$), and time to $C_{max}$ ($T_{max}$), elimination half-life ($t_{1/2}$) and terminal elimination rate constant ($K_{el}$).

Relative Bioavailability Comparison of Test Vs. Reference Formulations:

The relative bioavailability of the Test and Reference formulations were compared; more specifically, the Test formulation—Colchicine Oral Solution 0.6 mg (0.12 mg/mL, 5 mL) was compared to the Reference formulation—Probenecid and Colchicine Tablets USP (500 mg/0.5 mg), with both formulations administered under fasted conditions. Plasma colchicine $C_{max}$ and AUC values were dose-normalized.

Results

The human clinical trial (Study-001) was a 3-way crossover study of Probenecid and Colchicine Tablets USP, 500/0.5 mg reference formulation in the fasted state following a 10-hour overnight fast vs. a single dose of Colchicine Oral Solution (i.e. liquid colchicine solution of the invention), 0.6 mg (0.12 mg/mL, 5 mL) test formulation in the fasted state following a 10-hour overnight fast vs. a single dose of Colchicine Oral Solution following a standard FDA high-fat meal.

Safety/Toxicity (Adverse Events) Results

A total of 36 human patients were randomized in the study, of which 34 subjects (94.4%) were included in the PK population and all 36 subjects (100%) were included in the safety population. Two (2) subjects (5.6%) discontinued prematurely from the study, one subject requested to be withdrawn from the study and the other was noncompliant with the study protocol. Single doses of Colchicine Oral Solution and Probenecid and Colchicine Tablets were safely administered and generally well tolerated in these healthy adult subjects.

PK Results

Mean colchicine plasma concentrations vs. time profiles are shown in FIG. 1 on a semi logarithmic scale. A summary of the PK parameters for colchicine is displayed in Table 1. Similar PK profiles suggest that colchicine absorption in the oral solution (Test) was similar to the tablet formulation (Reference). Median $T_{max}$ for the oral solution was the same as the tablet formulation (1 hour). The apparent terminal half-life (31 hours) of colchicine oral solution was also similar to the tablet formulation (31 hours). Dose-normalized colchicine mean $C_{max}$ for Treatment A (3.60 ng/mL) was similar to the dose-normalized $C_{max}$ for Treatment C (3.66 ng/mL). Dose-normalized colchicine mean $AUC_{0-t}$ for Treatment A (31.0 h·ng/mL/mg) was similar to that of Treatment C (31.1 h·ng/mL/mg). In the fed state, median $T_{max}$ increased to 2 hours compared to 1 hour in the fasted state. The mean $C_{max}$ was 78.0% when comparing fed state to fasted state and the mean $AUC_{0-t}$ was 92.5% when comparing fed state to fasted state.

TABLE 1

Summary of PK Parameters by Treatment - PK Population

| Parameter | Statistic | Colchicine Oral Solution, 0.6 mg (0.12 mg/mL, 5 mL) | Colchicine Oral Solution, 0.6 mg (0.12 mg/mL, 5 mL) | Probenecid and Colchicine Tablets, 500 mg/0.5 mg Fasted (N = 34) |
|---|---|---|---|---|
| $AUC_{0-t}$ (h · ng/mL) | Mean (SD) | 18.59 (4.635) | 17.20 (4.231) | 15.54 (5.021) |
| $AUC_{0-t}$/Dose (h · ng/mL/mg) | Mean (SD) | 30.98 (7.726) | 28.67 (7.052) | 31.07 (10.04) |
| $AUC_{0-inf}$ (h · ng/mL) | Mean (SD) | 19.90 (4.736) | 18.47 (4.290) | 16.70 (4.988) |
| $AUC_{0-inf}$/Dose (h*ng/mL/mg) | Mean (SD) | 33.18 (7.897) | 30.79 (7.162) | 33.40 (9.985) |
| $C_{max}$ (ng/mL) | Mean (SD) | 2.161 (0.8741) | 1.685 (0.3945) | 1.828 (0.7096) |
| $C_{max}$/Dose (ng/mL/mg) | Mean (SD) | 3.602 (1.457) | 2.809 (0.6575) | 3.655 (1.419) |
| $T_{max}$ (h) | Median (Min-Max) | 1.00 (0.50: 2.00) | 2.00 (1.00: 4.00) | 1.00 (0.50: 1.75) |
| $t_{1/2}$ (h) | Mean (SD) | 31.04 (5.988) | 30.54 (5.219) | 31.20 (6.770) |
| $K_{el}$ (1/h) | Mean (SD) | 0.0232 (0.0049) | 0.0233 (0.0036) | 0.0231 (0.0046) |

A: Colchicine Oral Solution 0.6 mg (0.12 mg/mL, 5 mL), Fasted;
B: Colchicine Oral solution 0.6 mg (0.12 mg/mL, 5 mL), Fed
C: Probenecid and Colchicine Tablets, 500 mg/0.5 mg, Fasted Bioavailability Results A summary of relative bioavailability analyses for Colchicine Oral Solution vs. tablets and Colchicine Oral Solution fasted vs. fed are displayed in Table 2 and Table 3, respectively. Dose-normalized relative bioavailability of colchicine oral solution was 101.2 (90% CI: 94.05-109.0) for $AUC_{0-t}$ ratio and 98.45% (90% CI: 88.47-109.6%) for $C_{max}$ ratio. With respect to the bioequivalence analysis of Treatment A vs. Treatment C, the 90% CIs for $C_{max}$, $AUC_{0-t}$ and $AUC_{0-inf}$ were contained within the pre-defined limit of 80 to 125% for colchicine.

TABLE 2

Summary of Dose Normalized Relative Bioavailability Analysis for Test vs. Reference of Colchicine - PK Population (Study-001)

| normalized | n | A | n | C | GMR A/C | 90% CI (%) A/C | Intra-Subject CV % |
|---|---|---|---|---|---|---|---|
| $C_{max}$/Dose (ng/mL/mg) | 34 | 3.356 | 34 | 3.408 | 98.45 | (88.47-109.6) | 26.86 |
| $AUC_{0-t}$/Dose (ng · hr/mL/mg) | 34 | 30.09 | 34 | 29.72 | 101.2 | (94.05-109.0) | 18.33 |
| $AUC_{0-inf}$/Dose (ng · hr/mL/mg) | 34 | 32.32 | 34 | 32.16 | 100.5 | (93.86-107.6) | 16.95 |

A: Colchicine Oral Solution 0.6 mg (0.12 mg/mL, 5 mL), Fasted
C: Probenecid and Colchicine Tablets, 500 mg/0.5 mg, Fasted

TABLE 3

Dose Normalized Food Effect Evaluation of Colchicine Test Formulation

| normalized | n | A | n | B | GMR B/A | 90% CI (%) B/A | Intra-Subject CV % |
|---|---|---|---|---|---|---|---|
| $C_{max}$/Dose (ng/mL/mg) | 34 | 3.356 | 34 | 2.731 | 81.37 | (73.12-90.55) | 26.86 |
| $AUC_{0-t}$/Dose (ng · hr/mL/mg) | 34 | 30.09 | 34 | 27.80 | 92.40 | (85.84-99.46) | 18.33 |
| $AUC_{0-inf}$/Dose (ng · hr/mL/mg) | 34 | 32.32 | 34 | 29.99 | 92.79 | (86.68-99.33) | 16.95 |

A: Colchicine Oral Solution 0.6 mg (0.12 mg/mL, 5 mL), Fasted
B: Colchicine Oral Solution 0.6 mg (0.12 mg/mL, 5 mL), Fed Conclusions The comparisons of colchicine exposure (dose normalized $C_{max}$, $AUC_{0-t}$ and $AUC_{0-inf}$) between the test (oral solution) and reference formulation (tablet) satisfied the bioequivalence criteria as $C_{max}$, $AUC_{0-t}$ and $AUC_{0-inf}$ GMRs were fully contained within the 80 to 125% boundaries. The study showed that a minimum food effect was observed when colchicine oral solution was administered following a high fat high calorie meal. A slight decrease in $C_{max}$ was observed; however, the overall extent of absorption, based on GMRs for $AUC_{0-t}$ and $AUC_{0-inf}$, was similar in the fed and fasted states.

Example 2: Study-002

Study-002 was an open-label, 2-period, sequential human clinical study to assess the effects of multiple oral doses of Coreg CR® (carvedilol phosphate) Extended-Release Capsules on the PK of a single oral dose of Colchicine Oral Solution, 0.6 mg (0.12 mg/mL, 5 mL) in healthy male and female adult volunteers. The study was designed to assess the effects of carvedilol phosphate, a known inhibitor of the P-gp transporter, on the PK of colchicine, a known P-gp substrate. The dosing scheme for this study is illustrated in Table 4. In each of the two treatment periods, serial PK blood samples to measure plasma concentrations of colchicine were collected prior to dosing (0 hour, up to 60 minutes prior to dosing) and at 0.5, 0.75, 1, 1.25, 1.5, 2, 3, 4, 6, 8, 12, 24, 36, 48, 72 and 96 hours post dose.

TABLE 4

Study-002 Dosing Scheme

| Period, Day | Treatments and PK Sampling Description |
|---|---|
| Period 1, Day 1 | Single oral dose of Colchicine Oral Solution, 0.6 mg (0.12 mg/mL, 5 mL) at approximately 08:00 hours administered 30 minutes following a standard breakfast |
| Period 1, Days 2 to 10 | Washout period between treatments |
| Period 2, Days 11 to 12 | Single daily oral doses of Coreg CR ® (carvedilol phosphate) Extended-Release Capsule, 20 mg at approximately 08:00 hours administered 30 minutes following a standard breakfast |
| Period 2, Days 13 to 16 | Single daily oral dose of Coreg CR ® (carvedilol phosphate) Extended-Release Capsule, 40 mg at approximately 08:00 hours each morning administered 30 minutes following a standard breakfast |
| Period 2, Day 17 | Single oral dose of Colchicine Oral Solution, 0.6 mg (0.12 mg/mL, 5 mL) with a single oral dose of Coreg CR ® (carvedilol phosphate) Extended-Release Capsule, 40 mg at approximately 08:00 hours administered 30 minutes following a standard breakfast |

A total of 24 healthy adult subjects were dosed on the study, of which 21 subjects (87.5%) completed study treatment per protocol; 3 subjects (12.5%) discontinued prematurely from the study due to positive drug screen, noncompliance with the protocol and withdrawal of consent. All 24 subjects (100.0%) were included in the safety and PK populations. Twenty-one (21) subjects (87.5%) were included in the drug-drug interaction (DDI) assessment of the Coreg CR® impact on the plasma PK of colchicine.

Safety/Toxicity (Adverse Events) Results

Single doses of Colchicine Oral Solution administered with and without carvedilol phosphate (Coreg CR®) were safely administered and generally well tolerated in these healthy adult subjects.

PK Results

Figure 2:
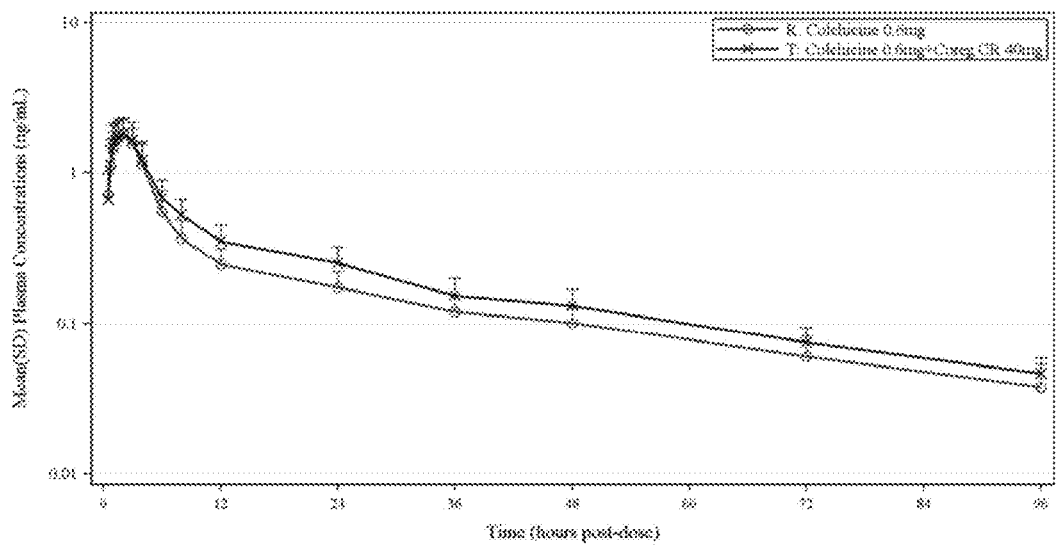
FIG. 2 is a graph depicting a determination of mean (SD) colchicine plasma concentrations (ng/mL) vs. time (Semi-log Scale)—PK Population in human clinical study 2 (Example 2).

Mean colchicine plasma concentrations vs. time profiles are shown in FIG. 2 on a semi-logarithmic scale. A summary of the PK parameters for colchicine is provided in Table 5.

Similar PK profiles were observed for Colchicine Oral Solution when administered alone and when co-administered with carvedilol phosphate. When colchicine was co-administered with carvedilol phosphate, the terminal phase profile was slightly higher than colchicine alone, but both terminal phase profiles were parallel. The median $t_{max}$ value for colchicine alone and with the concomitant use of carvedilol phosphate was the same. The apparent terminal half-life (~31 hours) of colchicine alone was also similar to the co-administration with carvedilol phosphate (~32 hours). The mean $C_{max}$ value for colchicine alone (1.973 ng/mL) was similar to the $C_{max}$ value for co-administration with carvedilol phosphate (1.920 ng/mL). Mean $AUC_{0-last}$ for colchicine co-administration with carvedilol phosphate (22.06 h·ng/mL) was 23% higher than that of colchicine alone (17.91 h·ng/mL).

Given that colchicine is a known substrate for P-gp, it is hypothesized that an inhibitor of P-gp such as carvedilol phosphate could potentially affect the PK profile of colchicine. In this study, it was surprisingly demonstrated that carvedilol phosphate had no effect on the $C_{max}$ of colchicine. The percent GMR of $AUC_{0-last}$ (co-administration with carvedilol phosphate/colchicine alone) was 117.9% and its 90% CI was in the range of 112.0%-124.1%. The 90% CIs for $C_{max}$, $AUC_{0-last}$ and $AUC_{0-inf}$ were contained within the 80 to 125% boundaries.

TABLE 5

Summary of Colchicine PK Parameters - PK Population

| Parameter | Statistic | Colchicine Oral Solution, 0.6 mg (0.12 mg/mL, 5 mL) (N = 24) | Colchicine Oral Solution, 0.6 mg (0.12 mg/mL, 5 mL) + Coreg CR ® 40 mg (N = 21) |
|---|---|---|---|
| $AUC_{0-last}$ (h*ng/mL) | Mean (SD) | 17.91 (4.169) | 22.06 (5.531) |
| $Ln(AUC_{0-last})$ | Mean (SD) | 2.858 (0.2413) | 3.061 (0.2697) |
| $AUC_{0-inf}$ (h*ng/mL) | Mean (SD) | 19.69 (4.523) | 24.23 (5.879) |
| $Ln(AUC_{0-inf})$ | Mean (SD) | 2.954 (0.2359) | 3.156 (0.2652) |
| $C_{max}$ (ng/mL) | Mean (SD) | 1.973 (0.4818) | 1.920 (0.5240) |
| $Ln(C_{max})$ | Mean (SD) | 0.6536 (0.2270) | 0.6178 (0.2690) |
| $T_{max}$ (h) | Median (Min-Max) | 2.00 (1.00, 4.00) | 2.00 (0.75, 3.00) |
| $AUC_{0-last}/AUC_{0-inf}$ (%) | Mean (SD) | 89.91 (5.441) | 90.96 (2.708) |
| Vz/F (L) | Mean (SD) | 1420 (329.9) | 1233 (405.3) |
| CL/F (L/h) | Mean (SD) | 32.12 (7.736) | 26.48 (7.835) |
| Kel (1/h) | Mean (SD) | 0.0230 (0.0043) | 0.0220 (0.0035) |
| $t_{1/2}$ (h) | Mean (SD) | 31.13 (5.560) | 32.22 (4.895) |

Effect of Carvedilol Phosphate on Colchicine PK Results

Carvedilol phosphate had no significant effect on the plasma $C_{max}$ and AUC parameters of colchicine (Table 6). The 90% CIs for $C_{max}$, $AUC_{0-last}$ and $AUC_{0-inf}$ were contained within the pre-defined 80 to 125% boundaries.

TABLE 6

Effect of Coreg CR ® (carvedilol phosphate) on the Plasma PK of Colchicine - DDI Assessment (Study-002)

| PK Parameter | Least Square Geometric Means | | | | GMR (%) T/R | GMR 90% CI (%) T/R | Intra-Subject CV % |
|---|---|---|---|---|---|---|---|
| | N | T | n | R | | | |
| $C_{max}$ (ng/mL) | 21 | 1.855 | 21 | 1.940 | 95.59 | (89.64-101.9) | 12.11 |
| $AUC_{0-last}$ (ng·h/mL) | 21 | 21.35 | 21 | 18.11 | 117.9 | (112.0-124.1) | 9.673 |

TABLE 6-continued

Effect of Coreg CR ® (carvedilol phosphate) on the
Plasma PK of Colchicine - DDI Assessment (Study-002)

| PK Parameter | Least Square Geometric Means | | | | GMR (%) T/R | GMR 90% CI (%) T/R | Intra-Subject CV % |
|---|---|---|---|---|---|---|---|
| | N | T | n | R | | | |
| $AUC_{0-inf}$ (ng · h/mL) | 19 | 23.54 | 19 | 19.99 | 117.8 | (111.8-124.0) | 9.220 |

R: Colchicine Oral Solution, 0.6 mg (0.12 mg/mL, 5 mL)
T: Colchicine Oral Solution, 0.6 mg (0.12 mg/mL, 5 mL) + Coreg CR ®, 40 mg Conclusions No significant drug interaction was observed for Colchicine Oral Solution when administered with the P-gp inhibitor, carvedilol phosphate, based on the 90% CIs for the $C_{max}$, $AUC_{0-last}$ and $AUC_{0-inf}$ GMRs being fully contained within the 80 to 125% bioequivalence boundaries.

Colchicine Oral Solution was well tolerated in the study when administered as a single oral 0.6 mg dose alone and in combination with multiple doses of carvedilol phosphate extended-release capsules. No safety concerns were raised during the study. No subject discontinued the study drug due to an AE. There were no SAEs reported in the study.

Example 3: Study-003

Study-003 was a three cohort, open-label, 2-period, sequential human clinical study to assess the effects of multiple oral doses of Noxafil® (posaconazole) Delayed Release Tablets, Cipro® (ciprofloxacin hydrochloride) Tablets, and Norvasc® (amlodipine besylate) tablets on the PK of a single oral dose of Colchicine Oral Solution, 0.6 mg (0.12 mg/mL, 5 mL) in healthy male and female adult volunteers. The study was designed to assess the effects of strong (posaconazole), moderate (ciprofloxacin hydrochloride) and weak (amlodipine besylate) CYP3A4 inhibitors, on the PK of colchicine, a known CYP3A4 substrate. The dosing scheme and serial blood PK sampling schedule for this study by period and cohort is outlined in Table 7.

TABLE 7

Study-003 Dosing Scheme and Sampling Schedule

| Period, Day | Cohort 1 | Cohort 2 | Cohort 3 |
|---|---|---|---|
| Period 1, Day 1 | Single oral dose of Colchicine Oral Solution, 0.6 mg (0.12 mg/mL, 5 mL) at approximately 08:00 hours administered 30 minutes following a light breakfast for Cohort 1 and following an overnight fast in Cohorts 2 and 3, such that dosing conditions relative to fed or fasted state are identical within a cohort for Periods 1 and 2. Serial PK samples for plasma colchicine concentration determination following Day 1 dosing will be obtained at 0, 0.5, 0.75, 1, 1.25, 1.5, 2, 3, 4, 6, 8, 12, 24, 36, 48, 72, and 96 hours postdose (Days 1, 2, 3, 4 and 5). | | |
| Period 1, Days 2 to 10 | Washout period between treatments | | |
| Period 2, Days 11to 16 for Cohorts 1 and 2, Days 11 to 19 for Cohort 3 | On Day 11, each subject will receive 300 mg Noxafil ® (posaconazole) (100 mg × 3) delayed-release tablets at 8:00 a.m. and 6:00 pm, then on Days 12-16, each subject will receive a 300 mg Noxafil ® (posaconazole) ® dose at 8:00 a.m. following a light breakfast. | On Days 11-16, each subject will receive one 500 mg Cipro ® (ciprofloxacin hydrochloride) tablet at 8:00 a.m. and at 8:00 p.m. in the fasted state, following an overnight fast of at least 10 hours. | On Days 11-13, each subject will receive a 5 mg Norvasc ® (amlodipine besylate) tablet at 8:00 a.m., then if tolerated based on vital signs assessments and overall safety and tolerability assessments, on Days 14-19, subjects will receive a 10 mg Norvasc ® (amlodipine besylate) tablet at 8:00 a.m. in the fasted state following an overnight fast of at least 10 hours. |
| Period 2, Day 17 for Cohorts 1 and 2, Day 20 for Cohort 3 | On Day 17, each subject will receive both one dose of 0.6 mg colchicine oral solution and a 300 mg Noxafil ® (posaconazole) (100 × 3) dose at 8:00 a.m. following a light breakfast. | On Day 17, each subject will receive both one dose of 0.6 mg colchicine oral solution and a 500 mg Cipro ® (ciprofloxacin hydrochloride)dose at 8:00 a.m. following an overnight fast of at least 10 hours and a final dose of Cipro ® 500 mg at 8:00 p.m. (without colchicine). | On Day 20, each subject will receive both one dose of 0.6 mg colchicine oral solution and a 10 mg Norvasc ® (amlodipine besylate) tablet dose at 8:00 a.m. in the fasted state following an overnight fast of at least 10 hours. |
| Period 2, serial PK sampling following last dose of Colchicine + CYP3A4 inhibitor | Serial PK samples for plasma colchicine concentration determination will be obtained following Day 17 dosing at 0, 0.5, 0.75, 1, 1.25, 1.5, 2, 3, 4, 6, 8, 12, 24, 36, 48, 72, and 96 hours postdose (Days 17, 18, 19, 20 and 21). | Serial PK samples for plasma colchicine concentration determination will be obtained following Day 17 dosing at 0, 0.5, 0.75, 1, 1.25, 1.5, 2, 3, 4, 6, 8, 12, 24, 36, 48, 72, and 96 hours postdose (Days 17, 18, 19, 20 and 21). | Serial PK samples for plasma colchicine concentration determination will be obtained following Day 20 dosing at 0, 0.5, 0.75, 1, 1.25, 1.5, 2, 3, 4, 6, 8, 12, 24, 36, 48, 72, and 96 hours postdose (Days 20, 21, 22, 23 and 24). |

1. Cohort 1: Effect of the Strong CYP3A4 Inhibitor (Posaconazole) on Colchicine PK A total of 24 healthy adult subjects were dosed in each cohort on the study. Twenty-two (22) subjects (91.7%) completed study treatment per protocol. Two (2) subjects (8.3%) discontinued prematurely from the study due to noncompliance with the protocol and withdrawal of consent. Twenty-four (100%) overall subjects were included in the safety and PK population; and twenty-two (22) (91.7%) subjects were included in the DDI assessment of the combined posaconazole and colchicine dosing.

Safety/Toxicity (Adverse Events) Results

Single doses of Colchicine Oral Solution administered with and without posaconazole (Noxafil®) were safely administered and generally well tolerated in these healthy adult subjects.

PK Results

Figure 3:
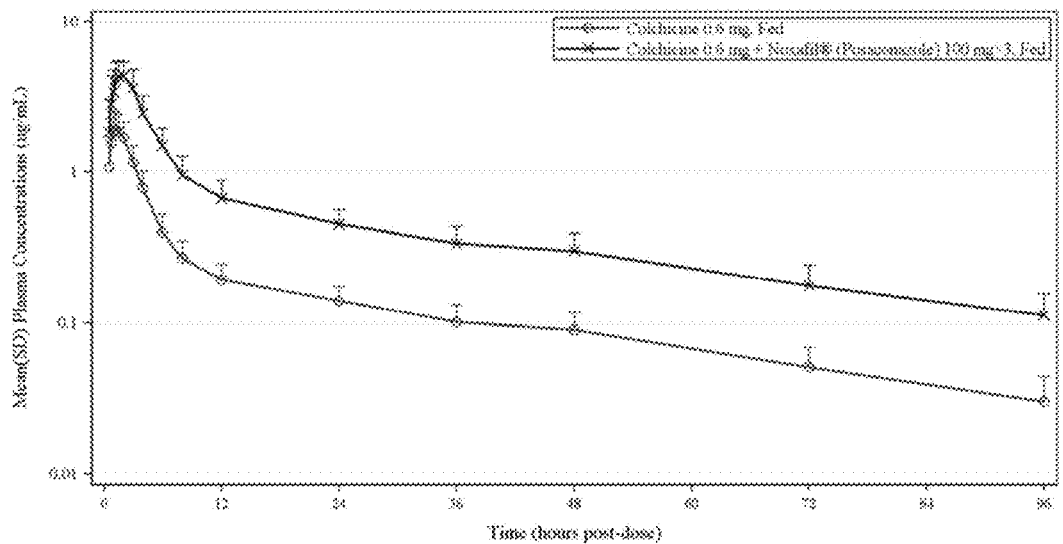
FIG. 3 is a graph depicting a determination of mean (SD) colchicine plasma concentrations (ng/mL) vs. time (Semi-log Scale)—PK Population in human clinical study 3 cohort 1 (Example 3).

The data with posaconazole is shown in FIG. 3 and Table 8. The GMR values and 90% CI's for $C_{max}$ and $AUC_{0-last}$ fell outside the 80 to 125% boundaries for bioequivalence (Table 9). The terminal half-life remained unchanged when Colchicine Oral Solution was administered alone (32.86 hours) or with posaconazole (32.51 hours). These results show that colchicine plasma levels are markedly elevated (by approximately 3.1 fold) in the presence of a strong CYP3A4 inhibitor. The combination of colchicine+posaconazole was generally well-tolerated, however due to the 3.1 fold increase in colchcine plasma levels, a dose adjustment to 2 mL daily is recommended when co-administering colchicine oral liquid and posaconazole.

TABLE 8

Summary of PK Parameters - PK Population (Study-003, Cohort 1 - Strong CYP3A4 Inhibitor: Posaconazole)

| Parameter | Statistic | Colchicine Oral Solution, 0.6 mg (0.12 mg/mL, 5 mL) Fed (N = 24) | Colchicine Oral Solution, 0.6 mg (0.12 mg/mL, 5 mL) + Noxafil ® (posaconazole), 300 mg (100 mg × 3) Fed (N = 22) |
|---|---|---|---|
| $AUC_{0-last}$ (h · ng/mL) | Mean (SD) | 15.28 (3.904) | 47.14 (13.50) |
| $Ln(AUC_{0-last})$ | Mean (SD) | 2.696 (0.2553) | 3.815 (0.2872) |
| $AUC_{0-inf}$ (h · ng/mL) | Mean (SD) | 16.92 (4.571) | 52.20 (16.03) |
| $Ln(AUC_{0-inf})$ | Mean (SD) | 2.795 (0.2661) | 3.911 (0.3077) |
| $C_{max}$ (ng/mL) | Mean (SD) | 2.053 (0.5749) | 4.670 (1.269) |
| $Ln(C_{max})$ | Mean (SD) | 0.6831 (0.2752) | 1.504 (0.2870) |
| $T_{max}$ (h) | Median (Min-Max) | 1.25 (0.75-3) | 1.50 (1-3) |
| $AUC_{\%inf}$ (%) | Mean (SD) | 89.85 (4.083) | 89.83 (3.643) |
| Vz/F (L) | Mean (SD) | 1775 (477.1) | 577.7 (161.9) |
| CL/F (L/h) | Mean (SD) | 37.96 (10.46) | 12.58 (4.145) |
| $K_{el}$ (/h) | Mean (SD) | 1.704 (0.9902) | 1.657 (0.9642) |
| $t_{1/2}$ (h) | Mean (SD) | 32.86 (5.308) | 32.51 (4.869) |

TABLE 9

Effect of Noxafil ® (Posaconazole) on the Plasma PK of Colchicine - Cohort 1 DDI Assessment (Study-003)

| PK Parameter | Least Square Geometric Means | | | | GMR (%) T/R | GMR 90% CI (%) T/R | Intra-Subject CV % |
|---|---|---|---|---|---|---|---|
| | n | T | n | R | | | |
| $C_{max}$ (ng/mL) | 22 | 4.498 | 22 | 1.980 | 227.1 | (201.6-255.8) | 23.26 |
| $AUC_{0-last}$ (ng · h/mL) | 22 | 45.36 | 22 | 14.60 | 310.7 | (283.7-340.4) | 17.69 |
| $AUC_{0-inf}$ (ng · h/mL) | 20 | 49.31 | 20 | 15.98 | 308.7 | (281.0-339.0) | 17.27 |

R: Colchicine Oral Solution, 0.6 mg (0.12 mg/mL, 5 mL), Fed
T: Colchicine Oral Solution, 0.6 mg (0.12 mg/mL, 5 mL) + Noxafil ® (posaconazole), 300 mg (100 mg × 3), Fed Conclusions (Cohort 1)

Colchicine Oral Solution was well tolerated in the study when administered as a single oral 0.6 mg dose alone and in combination with multiple doses of posaconazole delayed-release tablets. No safety concerns were raised during the study. No subject discontinued the study d rug due to an AE. There were no SAEs reported in the study.

The combination of colchicine+posaconazole was well tolerated, however due to the 3.1 fold increase in colchicine plasma levels an initial dose adjustment for colchicine is recommended when co-administering colchicine with posaconazole.

2. Cohort 2: Effect of the Moderate CYP3A4 Inhibitor Ciprofloxacin Hydrochloride on Colchicine PK Twenty (20) subjects (83.3%) completed study treatment per protocol. Four subjects (16.7%) discontinued prematurely from the study; 3 subjects withdrew consent for personal reasons and one subject was discontinued based on the investigator's conclusion that ciprofloxacin hydrochloride was not being tolerated. Twenty-four (100%) overall subjects were included in the safety and PK population; and twenty (20) (83.3%) subjects were included in the DDI assessment of the combined ciprofloxacin hydrochloride and colchicine dosing.

Safety/Toxicity (Adverse Events) Results

Single doses of Colchicine Oral Solution administered with and without ciprofloxacin hydrochloride (Cipro®) were safely administered and generally well tolerated in these healthy adult subjects.

PK Results

Figure 4:
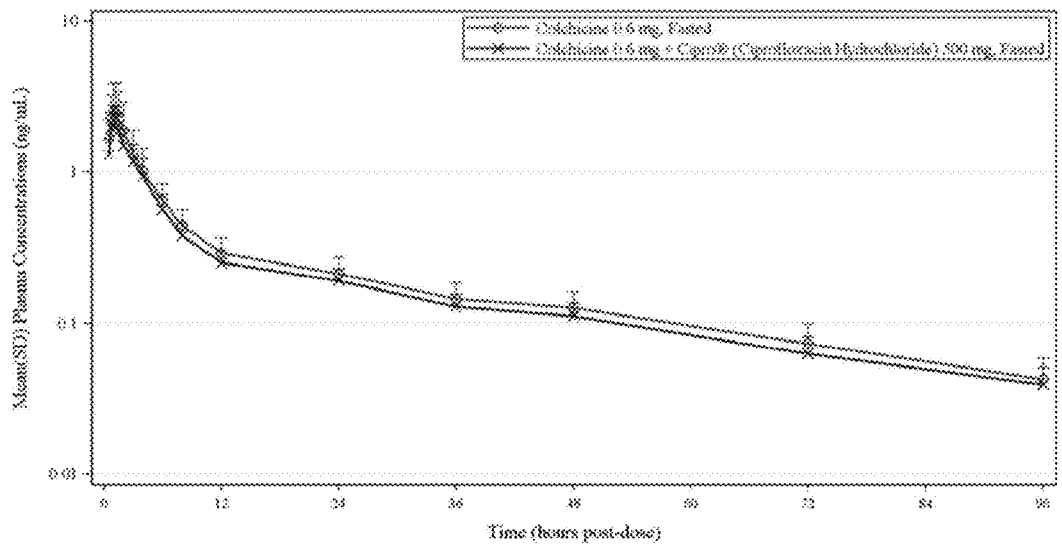
FIG. 4 is a graph depicting a determination of mean (SD) colchicine plasma concentrations (ng/mL) vs. time (Semi-log Scale)—PK Population in human clinical study 3 cohort 2 (Example 3).

As shown in FIG. 4 and Table 10, ciprofloxacin hydrochloride had no marked effects on the mean $C_{max}$, $AUC_{0\text{-}last}$ and terminal half-life of Colchicine Oral Solution. The GMR values and 90% CI's for $C_{max}$ and $AUC_{0\text{-}last}$ fell within the 80 to 125% boundaries for bioequivalence (Table 11) indicating that a drug-drug interaction with the moderate CYP3A4 ciprofloxacin hydrochloride was unlikely.

TABLE 10

Summary of PK Parameters - PK Population (Study-003, Cohort 2)

| Parameter | Statistic | Colchicine Oral Solution, 0.6 mg (0.12 mg/mL, 5 mL) Fasted (N = 24) | Colchicine Oral Solution, 0.6 mg (0.12 mg/mL, 5 mL) + Cipro ® (ciprofloxacin hydrochloride), 500 mg Fasted (N = 20) |
|---|---|---|---|
| $AUC_{0\text{-}last}$ (h · ng/mL) | Mean (SD) | 21.32 (6.585) | 18.49 (3.431) |
| $Ln(AUC_{0\text{-}last})$ | Mean (SD) | 3.014 (0.3127) | 2.901 (0.1860) |
| $AUC_{0\text{-}inf}$ (h · ng/mL) | Mean (SD) | 23.38 (7.085) | 20.30 (3.940) |
| $Ln(AUC_{0\text{-}inf})$ | Mean (SD) | 3.107 (0.3084) | 2.993 (0.1972) |
| $C_{max}$ (ng/mL) | Mean (SD) | 2.689 (1.396) | 2.331 (0.6933) |
| $Ln(C_{max})$ | Mean (SD) | 0.8865 (0.4438) | 0.8067 (0.2844) |
| $T_{max}$ (h) | Median (Min-Max) | 1.00 (0.5-1.5) | 1.00 (0.75-1.5) |
| $AUC_{t/inf}$ (%) | Mean (SD) | 91.10 (2.289) | 91.03 (4.115) |
| Vz/F (L) | Mean (SD) | 1284 (378.1) | 1332 (334.9) |
| CL/F (L/h) | Mean (SD) | 28.12 (9.225) | 30.66 (6.123) |
| $K_{el}$ (/h) | Mean (SD) | 0.0221 (0.0035) | 0.0237 (0.0048) |
| $t_{1/2}$ (h) | Mean (SD) | 31.98 (4.445) | 30.49 (6.511) |

TABLE 11

Effect of Cipro ® (ciprofloxacin hydrochloride) on the Plasma PK of Colchicine - Cohort 2 DDI Assessment (Study-003)

| PK Parameter | Least Square Geometric Means | | | | GMR (%) T/R | GMR 90% CI (%) T/R | Intra-Subject CV % |
|---|---|---|---|---|---|---|---|
| | n | T | n | R | | | |
| $C_{max}$ (ng/mL) | 20 | 2.241 | 20 | 2.556 | 87.65 | (74.25-103.5) | 31.06 |
| $AUC_{0\text{-}last}$ (ng · h/mL) | 20 | 18.19 | 20 | 20.87 | 87.16 | (78.02-97.37) | 20.47 |
| $AUC_{0\text{-}inf}$ (ng · h/mL) | 19 | 19.94 | 19 | 22.68 | 87.92 | (78.69-98.23) | 19.90 |

R: Colchicine Oral Solution, 0.6 mg (0.12 mg/mL, 5 mL), Fasted
T: Colchicine Oral Solution, 0.6 mg (0.12 mg/mL, 5 mL) + Cipro ® (ciprofloxacin hydrochloride), 500 mg, Fasted Conclusions (Cohort 2)

Colchicine Oral Solution was well tolerated in the study when administered as a single oral 0.6 mg dose alone and in combination with multiple doses of ciprofloxacin hydrochloride tablets. No safety concerns were raised during the study. No subject discontinued the study drug due to an AE. There were no SAEs reported in the study.

3. Cohort 3: Effect of the Weak CYP3A4 Inhibitor Amlodipine Besylate on Colchicine PK Twenty-one (21) subjects (87.5%) completed study treatment per protocol. Three subjects (12.5%) discontinued prematurely from the study due to investigators decision and withdrawal of consent. Twenty-four (100%) overall subjects were included in the safety and PK population; and twenty-one (21) (87.5%) subjects were included in the DDI assessment of the combined amlodipine besylate and colchicine dosing.

Safety/Toxicity (Adverse Events) Results

Single doses of Colchicine Oral Solution administered with and without amlodipine besylate (Norvasc®) were safely administered and well tolerated in these healthy adult subjects. There were no TEAEs when colchicine was co-administered with amlodipine besylate.

PK Results

Figure 5:
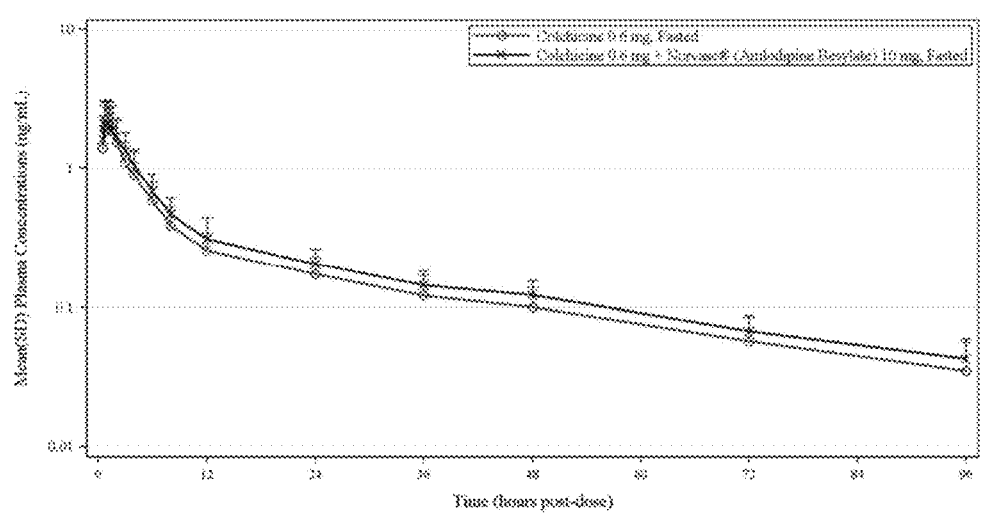
FIG. 5 is a graph depicting a determination of mean (SD) colchicine plasma concentrations (ng/mL) vs. time (Semi-log Scale)—PK Population in human clinical study 3 cohort 3 (Example 3).

As shown in FIG. 5 and Table 12, amlodipine besylate had a modest effect on the mean $C_{max}$ and $AUC_{0\text{-}last}$ of Colchicine Oral Solution. Plasma colchicine $C_{max}$, $AUC_{0\text{-}last}$ and $AUC_{0\text{-}inf}$ GMRs were approximately 1.09, 1.23 and 1.22-fold higher for colchicine+amlodipine besylate compared to colchicine alone.

The upper 90% CI's for $C_{max}$, $AUC_{0\text{-}last}$ and $AUC_{0\text{-}inf}$ fell outside the 80 to 125% boundaries for bioequivalence (Table 13) indicating that a drug-drug interaction with the weak CYP3A inhibitor amlodipine besylate could not be completely ruled out.

TABLE 12

Summary of PK Parameters - PK Population (Study-003, Cohort 3)

| Parameter | Statistic | Colchicine Oral Solution, 0.6 mg (0.12 mg/mL, 5 mL) Fasted (N = 24) | Colchicine Oral Solution, 0.6 mg (0.12 mg/mL, 5 mL) + Norvasc ® (amlodipine besylate) 10 mg Fasted (N = 21) |
|---|---|---|---|
| $AUC_{0\text{-}last}$ (h · ng/mL) | Mean (SD) | 17.83 (6.496) | 20.87 (4.954) |
| $Ln(AUC_{0\text{-}last})$ | Mean (SD) | 2.821 (0.3490) | 3.010 (0.2466) |
| $AUC_{0\text{-}inf}$ (h · ng/mL) | Mean (SD) | 19.84 (7.253) | 22.84 (5.406) |

TABLE 12-continued

Summary of PK Parameters - PK Population (Study-003, Cohort 3)

| Parameter | Statistic | Colchicine Oral Solution, 0.6 mg (0.12 mg/mL, 5 mL) Fasted (N = 24) | Colchicine Oral Solution, 0.6 mg (0.12 mg/mL, 5 mL) + Norvasc ® (amlodipine besylate) 10 mg Fasted (N = 21) |
|---|---|---|---|
| Ln(AUC$_{0-inf}$) | Mean (SD) | 2.929 (0.3469) | 3.101 (0.2409) |
| C$_{max}$ (ng/mL) | Mean (SD) | 2.183 (1.018) | 2.257 (0.9128) |
| Ln(C$_{max}$) | Mean (SD) | 0.6850 (0.4451) | 0.7414 (0.3875) |
| T$_{max}$ (h) | Median (Min-Max) | 1.00 (0.75-1.5) | 1.00 (0.75-4) |
| AUC$_{inf}$ (%) | Mean (SD) | 89.95 (4.231) | 90.61 (5.173) |
| Vz/F (L) | Mean (SD) | 1618 (661.8) | 1275 (491.2) |
| CL/F (L/h) | Mean (SD) | 33.93 (11.43) | 27.76 (6.808) |
| K$_{el}$ (/h) | Mean (SD) | 0.0218 (0.0048) | 0.0230 (0.0046) |
| t$_{1/2}$ (h) | Mean (SD) | 33.34 (7.603) | 31.46 (6.869) |

TABLE 13

Effect of Norvasc ® (amlodipine besylate) on the Plasma PK of Colchicine - Cohort 3 DDI Assessment (Study-003)

| | Least Square Geometric | | | GMR (%) | GMR 90% CI (%) | Intra-Subject |
|---|---|---|---|---|---|---|
| | n | T | n | R | T/R | T/R | CV % |
| C$_{max}$ (ng/mL) | 21 | 2.099 | 21 | 1.921 | 109.2 | (93.52-127.6) | 29.83 |
| AUC$_{0-last}$ (ng · h/mL) | 21 | 20.29 | 21 | 16.46 | 123.3 | (110.8-137.1) | 20.26 |
| AUC$_{0-inf}$ (ng · h/mL) | 20 | 22.23 | 20 | 18.27 | 121.7 | (109.1-135.7) | 20.15 |

R: Colchicine, 0.6 mg, Fasted
T: Colchicine, 0.6 mg + Norvasc ® (amlodipine besylate), 10 mg, Fasted Conclusions (Cohort 3)

A small increase in exposure was observed when Colchicine Oral Solution was administered with the weak CYP3A4 inhibitor, amlodipine besylate.

Plasma colchicine C$_{max}$, AUC$_{0-last}$ and AUC$_{0-inf}$ GMRs were approximately 1.09, 1.23 and 1.22-fold higher, respectively, for colchicine+amlodipine besylate compared to colchicine alone. Although the increase was surprising, the magnitude of this effect is small and dose adjustment for colchicine is not necessary when colchicine is administered with the weak CYP3A4 inhibitor amlodipine besylate.

Colchicine Oral Solution was well tolerated in the study when administered as a single, oral, 0.6 mg dose alone and in combination with multiple doses of amlodipine besylate tablets. No safety concerns were raised during the study. No subject discontinued the study drug due to an AE. There were no SAEs reported in the study.

Conclusions of Drug Interaction Studies

The pharmacokinetics of Colchicine Oral Solution were evaluated in the study following coadministration with posaconazole (a strong CYP3A4 inhibitor), ciprofloxacin hydrochloride (a moderate CYP3A inhibitor), amlodipine besylate (a weak CYP3A4 inhibitor) and carvedilol phosphate (a P-gp inhibitor) to determine the effects of co-administration. The results were quite surprising. The blood levels of colchicine have been demonstrated to be affected by the administration of colchicine in tablet or capsule form in combination with other drugs. The results vary widely based on the drugs, but the levels of colchicine may be shifted into toxic levels. Significantly, the levels of colchicine when combined with other drugs such as CYP34A inhibitors and P-g inhibitors, remained fairly stable, except for the combination with a strong CYP3A4 inhibitor, which caused a spike in colchicine to surprisingly high levels. These results were unexpected.

The combination of liquid colchicine with a strong CYP3A4 inhibitor produced mean colchicine C$_{max}$ values that were elevated by approximately 2.3-fold from 2.053 ng/mL (alone) to 4.670 ng/mL (with posaconazole) and mean AUC$_{0-last}$ values were elevated approximately 3.1-fold from 15.28 h·mg/mL (alone) to 47.14 h·ng/mL (with posaconazole). The terminal half-life remained unchanged when Colchicine Oral Solution was administered alone (32.86 hours) or with posaconazole (32.51 hours). The combination of colchicine+posaconazole was generally well tolerated, however due to the increase in colchicine plasma levels, an initial dose adjustment for colchicine is recommended when coadministering colchicine with posaconazole.

The combination of liquid colchicine with a moderate CYP3A4 inhibitor, Ciprofloxacin hydrochloride, resulted in no marked effects on the mean C$_{max}$, AUC$_{0-last}$ and terminal half-life of Colchicine Oral Solution. These results indicate that significant interactions with the moderate CYP3A inhibitor ciprofloxacin hydrochloride are unlikely.

The combination of liquid colchicine with a weak CYP3A4 inhibitor, Amlodipine besylate had a modest effect on the mean C$_{max}$ (approximately a 1.17-fold increase) and AUC$_{0-last}$ (approximately a 1.15-fold increase) of Colchicine Oral Solution. These results indicate that significant interactions with the weak CYP3A inhibitor amlodipine besylate are unlikely.

The combination of liquid colchicine with carvedilol phosphate had no effect on the C$_{max}$ of colchicine. The geometric mean percent ratio of AUC$_{0-last}$ (coadministration with carvedilol phosphate/colchicine alone) was 117.9% and its 90% CI was in the range of 112.0% to 124.1%. The 90% CIs for C$_{max}$, AUC$_{0-last}$ and AUC$_{0-inf}$ were contained within the 80.00 to 125.00% limits. These results indicate that an interaction with carvedilol phosphate is unlikely.

Example 4: Safety/Toxicity (Adverse Events) and Efficacy of Liquid Colchicine Solution Colchicine's effectiveness as a treatment for gout has been postulated to be due to its ability to block neutrophil-mediated inflammatory responses induced by monosodium urate crystals in synovial fluid. Colchicine disrupts the polymerization of β-tubulin into microtubules, thereby preventing the activation, degranulation, and migration of neutrophils to sites of inflammation. Colchicine also interferes with the inflammasome complex found in neutrophils and monocytes that mediates interleukin-1β (IL-1β) activation.

Colchicine is estimated to be effective at doses of approximately 0.015 mg/kg, toxic at doses greater than 0.1 mg/kg, and typically lethal at doses of approximately 0.8 mg/kg. In the therapeutic range, plasma 1 vels are in the range of approximately 0.5 to 3 ng/mL.

1. Adverse Reactions

Based on the current FDA-approved labeling for colchicine products, the most common and frequently reported adverse events of colchicine are gastrointestinal, including nausea, vomiting, abdominal pain and diarrhea which are reversible with discontinuation of colchicine.

The following adverse events have been reported with Probenecid and Colchicine Tablets USP:

1. Digestive: abdominal cramping, abdominal pain, diarrhea, lactose intolerance, nausea, vomiting, fever
2. Neurological: headache, dizziness, peripheral neuritis
3. Dermatological: alopecia, purpura, rash, pruritus
4. Hematological: anemia, leukopenia, granulocytopenia, thrombocytopenia, pancytopenia, aplastic anemia
5. Hepatobiliary: Elevated AST/ALT
6. Musculoskeletal: myotonia, muscle weakness, muscular pain
7. Reproductive: azoospermia, oligospermia Overdose toxicity can include severe allergic reactions and anaphylaxis, bone marrow suppression, cardiovascular collapse, renal failure, rhabdomyolysis, seizures, mental status changes and death.

2. Safety/Toxicity (Adverse Events) of Colchicine Oral Solution

Colchicine Oral Solution was well tolerated when administered orally as 0.6 mg in 5 mL to healthy adult male and female subjects in the bioavailability study (Example 1) and DDI studies (Examples 2 and 3).

The most common treatment-emergent adverse event TEAEs included headache, dizziness and nasal congestion. All TEAEs were of mild intensity, except for one TEAE of viral infection which was moderate in intensity and considered unlikely to be related to study drug. The majority of TEAEs were resolved at the end of the study, except for:

1. one report of a mild UTI, which was assessed as being unlikely related to study drug; and
2. one subject with a mildly elevated liver enzyme test (AST) reported at the exit visit (4 days after the last dose of study drugs), which was assessed by as possibly related to study drug.

No subject discontinued from the studies due to an AE, and there were no SAEs or deaths reported during the studies.

Table 4 represents a summary of the data obtained in human subjects treated with 0.6 mg colchicine prior to co-administering respective drugs for drug-to-drug interaction studies in comparison to published human clinical trial data for tablet and capsule formulations of colchicine, as detailed below.

TABLE 14

| Least Square Geometric Means | | | |
| --- | --- | --- | --- |
| Dosage Form | Cmax (ng/mL) | AUCo-t (ng · hr/mL) | AUCo-inf (ng · hr/mL) |
| Tablets** | 2.48 | 10.94 | 13.05 |
| Capsules*** | 2.24 | 16.98 | 19.62 |

TABLE 14-continued

| Least Square Geometric Means | | | |
| --- | --- | --- | --- |
| Dosage Form | Cmax (ng/mL) | AUCo-t (ng · hr/mL) | AUCo-inf (ng · hr/mL) |
| Oral Solution**** | 2.10 | 17.51\ | 19.23 |

**Represents mean values from treatment 1 for 9-drug-to-drug interaction studies conducted for Colcrys ® reported in www.clinicaltrials.gov (study numbers 16, 17, 27, 28, 30, 31, 33, 35, 37 and 39). Total subjects 197.
***Represents mean values from treatment 1 for 4-drug-to-drug interaction studies conducted for Mitigare ® reported in U.S. Pat. No. 9,555,029 B2. Total subjects 48.
****Represents mean values from treatment 1 for 4-drug-to-drug interaction studies conducted for Colchicine Oral Solution (0.12 mg/mL, 5 mL dose) by Romeg Therapeutics, LLC. Total subjects 84.

Table 15 depicts relative adverse events observed in human subjects treated with 0.6 mg colchicine prior to co-administering respective drugs for drug-to-drug interaction studies in comparison to published human clinical trial data for tablet and capsule formulations of colchicine.

TABLE 15

| Relative Adverse Events from Different Colchicine Dosage Forms | | | |
| --- | --- | --- | --- |
| Dosage form | Tablets | Capsules | Oral Solution |
| Total number of drug-to-drug interaction studies | 9 | 4 | 4 |
| Total number of subjects analyzed | 214 | 48 | 96 |
| Total number of subjects reporting adverse events | 41 | 26 | 9 |
| % of subjects affected with adverse events | 19.16 | 54.17 | 9.38 |
| Total number of adverse events reported | 70 | 57 | 10 |
| Number of adverse events/subject | 0.33 | 1.19 | 0.10 |

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method of treating a colchicine sensitive disorder, comprising orally administering a liquid colchicine solution to a human subject having a colchicine sensitive disorder in an effective amount to treat the disorder, wherein the colchicine sensitive disorder is selected from gout, familial Mediterranean fever (FMF), pericarditis, Behçet's disease, atrial fibrillation, amyloidosis, calcium pyrophosphate deposition disease (pseudogout), cirrhosis of the liver, or sarcoid arthritis, wherein the liquid colchicine solution comprises a concentration of colchicine of 0.01-1.0 mg/ml, 0.1-0.3% w/v of anhydrous citric acid, 0.8-1.6% w/v of dibasic sodium phosphate heptahydrate, 0.1-0.2% w/v of a thickening agent, a preservative, glycols, and water, and wherein the liquid colchicine solution is stable for at least one month at refrigerated and ambient temperature conditions.

2. The method of claim 1, wherein the liquid colchicine solution further comprises one or more agents selected from the group consisting of propylene glycol, glycerin, benzyl alcohol, xanthan gum, sucralose, a dye, and a flavoring agent and/or taste enhancing agent.

3. The method of claim 1, wherein the liquid colchicine solution has a stable pH.

4. The method of claim 1, wherein the liquid colchicine solution has a viscosity in the range of 40-800 cps.

5. The method of claim 1, wherein the liquid colchicine solution has less than 5% of total impurities.

6. The method of claim 1, wherein the liquid colchicine solution has less than 0.5% of degradants.

7. The method of claim 6, wherein the degradants comprise β-lumicolchicine, γ-lumicolchicine, and/or colchiceine.

8. The method of claim 1, wherein the liquid colchicine solution is a 0.12 mg/ml solution.

9. A method of treating gout, comprising orally administering a liquid colchicine solution to a human subject in an effective amount to treat gout, wherein the liquid colchicine solution comprises a concentration of colchicine of 0.01-1.0 mg/ml, 0.1-0.3% w/v of anhydrous citric acid, 0.8-1.6% w/v of dibasic sodium phosphate heptahydrate, 0.1-0.2% w/v of a thickening agent, a preservative, glycols, and water, and wherein the liquid colchicine solution is stable for at least one month at refrigerated and ambient temperature conditions.

10. The method of claim 9, wherein the liquid colchicine solution is a 0.12 mg/ml solution.

* * * * *